(12) United States Patent
Schneider et al.

(10) Patent No.: US 8,128,677 B2
(45) Date of Patent: Mar. 6, 2012

(54) DEVICE AND METHOD FOR TACKING PLAQUE TO A BLOOD VESSEL WALL

(75) Inventors: Peter Schneider, Honolulu, HI (US); Robert Giasolli, Honolulu, HI (US)

(73) Assignee: Intact Vascular LLC, Wayne, PA (US)

( * ) Notice: Subject to any disclaimer, the term of this patent is extended or adjusted under 35 U.S.C. 154(b) by 441 days.

(21) Appl. No.: 12/483,193

(22) Filed: Jun. 11, 2009

(65) Prior Publication Data
US 2010/0262225 A1 Oct. 14, 2010

Related U.S. Application Data

(63) Continuation-in-part of application No. 11/955,331, filed on Dec. 12, 2007, now Pat. No. 7,896,911.

(51) Int. Cl.
*A61F 2/06* (2006.01)
(52) U.S. Cl. .................. 623/1.11; 227/176.1
(58) Field of Classification Search .............. None
See application file for complete search history.

(56) References Cited

U.S. PATENT DOCUMENTS 3,221,746 A 12/1965 Noble
(Continued)

FOREIGN PATENT DOCUMENTS
WO W003101310 12/2003
(Continued)

OTHER PUBLICATIONS

Mosseri M, Rozenman Y, Mereuta A, Hasin Y, Gotsman M., "New Indicator for Stent Covering Area", in *Catheterization and Cardiovascular Diagnosis*, 1998, v. 44, pp. 188-192.

(Continued)

*Primary Examiner* — Gary Jackson
*Assistant Examiner* — Christopher Schubert
(74) *Attorney, Agent, or Firm* — Knobbe Martens Olson & Bear LLP

(57) ABSTRACT

A tack device for holding plaque against blood vessel walls in treating atherosclerotic occlusive disease is formed as a thin, annular band of durable, flexible material having a plurality of barbs or anchoring points on its outer annular periphery. The annular band has a length in the axial direction of the blood vessel walls that is about equal to or less than its diameter as installed in the blood vessel. In a preferred embodiment, the tack device is formed as a compressible metallic mesh band having outer barbs on outer sides of the mesh structure. Another embodiment may have a plurality of compressible mesh bands may be formed spaced apart coaxially from each other and connected by longitudinally extending bridge members. A preferred method is to perform angioplasty with a drug eluting balloon as a first step, and if there is any dissection to the blood vessel caused by the balloon angioplasty, one or more tack devices may be installed to tack down the dissected area of the blood vessel surface, in order to avoid the need to install a stent and thereby maintain a 'stent-free' environment.

12 Claims, 18 Drawing Sheets

U.S. PATENT DOCUMENTS

| | | | |
|---|---|---|---|
| 3,635,223 A | 1/1972 | Klieman | |
| 4,292,974 A * | 10/1981 | Fogarty et al. | 606/194 |
| 4,446,867 A * | 5/1984 | Leveen et al. | 606/194 |
| 4,465,072 A | 8/1984 | Taheri | |
| 4,515,587 A * | 5/1985 | Schiff | 600/18 |
| 4,545,367 A * | 10/1985 | Tucci | 128/898 |
| 4,545,390 A * | 10/1985 | Leary | 600/462 |
| 4,552,127 A * | 11/1985 | Schiff | 600/18 |
| 4,589,412 A * | 5/1986 | Kensey | 606/159 |
| 4,641,654 A * | 2/1987 | Samson et al. | 606/192 |
| 4,651,738 A * | 3/1987 | Demer et al. | 606/194 |
| 4,723,550 A * | 2/1988 | Bales et al. | 606/108 |
| 4,723,936 A * | 2/1988 | Buchbinder et al. | 604/95.01 |
| 4,723,938 A * | 2/1988 | Goodin et al. | 604/97.02 |
| 4,726,374 A * | 2/1988 | Bales et al. | 606/108 |
| 4,758,223 A * | 7/1988 | Rydell | 604/97.02 |
| 4,762,130 A * | 8/1988 | Fogarty et al. | 606/159 |
| 4,781,192 A * | 11/1988 | Demer | 606/195 |
| 4,784,636 A * | 11/1988 | Rydell | 604/22 |
| 4,846,174 A * | 7/1989 | Willard et al. | 606/194 |
| 4,848,342 A * | 7/1989 | Kaltenbach | 606/198 |
| RE33,166 E * | 2/1990 | Samson | 606/194 |
| 5,009,659 A * | 4/1991 | Hamlin et al. | 606/159 |
| 5,024,668 A * | 6/1991 | Peters et al. | 606/194 |
| 5,042,707 A | 8/1991 | Taheri | |
| 5,047,015 A * | 9/1991 | Foote et al. | 604/99.01 |
| 5,102,390 A * | 4/1992 | Crittenden et al. | 604/103.1 |
| 5,196,024 A | 3/1993 | Barath | |
| 5,201,757 A * | 4/1993 | Heyn et al. | 606/198 |
| 5,246,420 A * | 9/1993 | Kraus et al. | 604/95.01 |
| 5,250,029 A * | 10/1993 | Lin et al. | 604/103.1 |
| 5,250,060 A * | 10/1993 | Carbo et al. | 606/159 |
| 5,263,962 A * | 11/1993 | Johnson et al. | 606/192 |
| 5,269,758 A * | 12/1993 | Taheri | 604/96.01 |
| 5,318,529 A * | 6/1994 | Kontos | 604/103.1 |
| 5,336,234 A | 8/1994 | Virgil | |
| 5,344,397 A * | 9/1994 | Heaven et al. | 604/95.01 |
| 5,383,890 A * | 1/1995 | Miraki et al. | 606/194 |
| 5,397,305 A * | 3/1995 | Kawula et al. | 604/96.01 |
| 5,423,851 A | 6/1995 | Samuels | |
| 5,501,689 A | 3/1996 | Green | |
| 5,536,252 A * | 7/1996 | Imran et al. | 604/101.02 |
| 5,540,659 A * | 7/1996 | Teirstein | 604/104 |
| 5,545,135 A * | 8/1996 | Iacob et al. | 604/103.1 |
| 5,569,272 A | 10/1996 | Reed | |
| 5,616,149 A | 4/1997 | Barath | |
| 5,665,116 A | 9/1997 | Chaisson | |
| 5,681,346 A | 10/1997 | Orth | |
| 5,746,764 A * | 5/1998 | Green et al. | 606/194 |
| 5,797,951 A | 8/1998 | Mueller | |
| 5,800,526 A | 9/1998 | Anderson | |
| 5,813,977 A * | 9/1998 | Hinchliffe et al. | 600/183 |
| 5,911,725 A * | 6/1999 | Boury | 606/108 |
| 5,968,068 A * | 10/1999 | Dehdashtian et al. | 606/192 |
| 5,972,023 A * | 10/1999 | Tanner et al. | 606/219 |
| 6,004,328 A * | 12/1999 | Solar | 623/1.11 |
| 6,007,543 A | 12/1999 | Ellis | |
| 6,009,614 A * | 1/2000 | Morales | 29/516 |
| 6,036,725 A | 3/2000 | Avellanet | |
| 6,053,943 A | 4/2000 | Edwin | |
| 6,090,135 A * | 7/2000 | Plaia et al. | 623/1.11 |
| 6,157,852 A * | 12/2000 | Selmon et al. | 600/407 |
| 6,165,199 A * | 12/2000 | Barbut | 606/200 |
| 6,197,013 B1 | 3/2001 | Reed | |
| 6,221,102 B1 | 4/2001 | Baker | |
| 6,241,667 B1 * | 6/2001 | Vetter et al. | 600/407 |
| 6,266,550 B1 * | 7/2001 | Selmon et al. | 600/407 |
| 6,290,728 B1 | 9/2001 | Phelps | |
| 6,312,444 B1 * | 11/2001 | Barbut | 606/200 |
| 6,371,962 B1 | 4/2002 | Ellis | |
| 6,409,863 B1 * | 6/2002 | Williams et al. | 156/198 |
| 6,475,237 B2 | 11/2002 | Drasler | |
| 6,491,707 B2 * | 12/2002 | Makower et al. | 606/157 |
| 6,692,504 B2 | 2/2004 | Kurz | |
| 6,810,882 B2 * | 11/2004 | Langberg et al. | 128/898 |
| 6,913,600 B2 * | 7/2005 | Valley et al. | 604/96.01 |
| 6,942,680 B2 | 9/2005 | Grayz | |
| 6,951,554 B2 * | 10/2005 | Johansen et al. | 604/509 |
| 7,007,698 B2 | 3/2006 | Thornton | |
| 7,087,088 B2 | 8/2006 | Berg et al. | |
| 7,169,163 B2 * | 1/2007 | Becker | 606/196 |
| 7,179,284 B2 | 2/2007 | Khosravi | |
| 7,270,673 B2 | 9/2007 | Yee | |
| 7,279,007 B2 * | 10/2007 | Nikolic et al. | 623/11.11 |
| 7,296,577 B2 * | 11/2007 | Lashinski et al. | 128/898 |
| 7,303,572 B2 | 12/2007 | Meisheimer | |
| 7,720,521 B2 * | 5/2010 | Chang et al. | 600/424 |
| 7,955,315 B2 * | 6/2011 | Feinberg et al. | 604/528 |
| 2002/0123790 A1 | 9/2002 | White | |
| 2003/0158595 A1 | 8/2003 | Randall et al. | |
| 2003/0191479 A1 | 10/2003 | Thornton | |
| 2004/0098077 A1 | 5/2004 | Gianotti | |
| 2004/0143287 A1 | 7/2004 | Konstantino | |
| 2004/0186551 A1 | 9/2004 | Kao et al. | |
| 2005/0010275 A1 | 1/2005 | Sahatjian | |
| 2005/0251164 A1 | 11/2005 | Gifford | |
| 2005/0288764 A1 | 12/2005 | Snow et al. | |
| 2006/0149349 A1 | 7/2006 | Garbe | |
| 2006/0200231 A1 | 9/2006 | O'Brien et al. | |

FOREIGN PATENT DOCUMENTS

WO  WO 03-101310  12/2003

OTHER PUBLICATIONS

Supplemental Office Action for Australian Application No. 2008335140 dated Apr. 21, 2011.

* cited by examiner

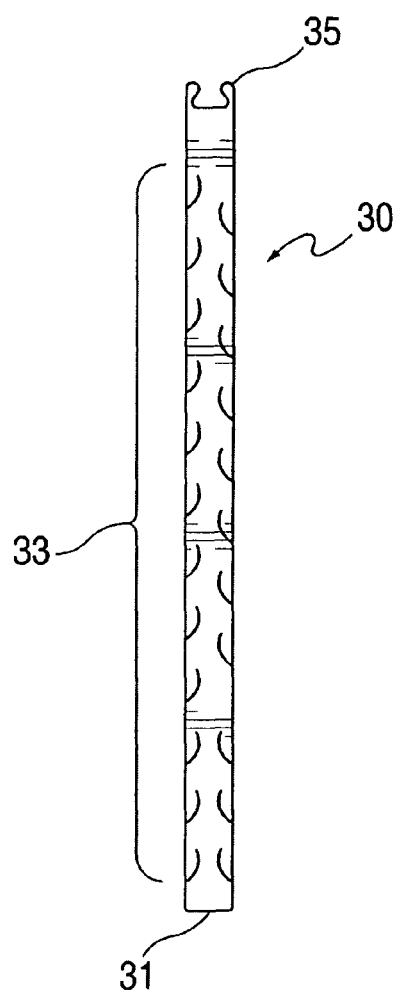
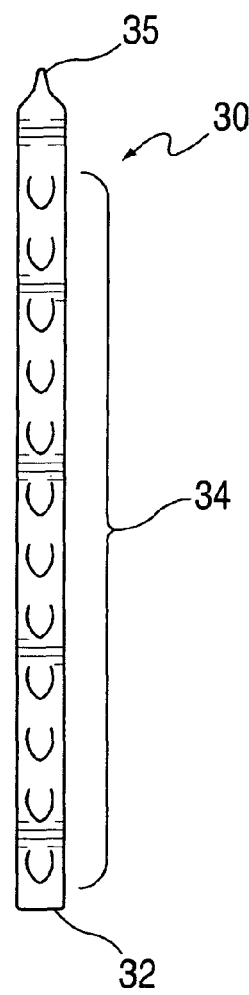
FIG. 1A  FIG. 1B
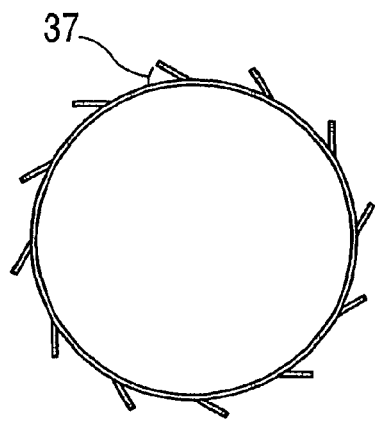
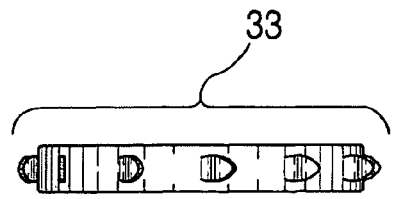
FIG. 2  FIG. 3

DEVICE AND METHOD FOR TACKING PLAQUE TO A BLOOD VESSEL WALL

This U.S. patent application is a continuation-in-part of U.S. patent application Ser. No. 11/955,331 of the same inventors, filed Dec. 12, 2007 now U.S. Pat. No. 7,896,911.

TECHNICAL FIELD

This invention relates to treatment of atherosclerotic occlusive disease by intravascular procedures for pushing and holding plaque accumulated on the blood vessel walls out of the way for reopened blood flow.

BACKGROUND OF INVENTION

Atherosclerotic occlusive disease is the primary cause of stroke, heart attack, limb loss, and death in the US and the industrialized world. Atherosclerotic plaque forms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is an accepted method of opening blocked or narrowed blood vessels in every vascular bed in the body. Balloon angioplasty is performed with a balloon angioplasty catheter. The balloon angioplasty catheter consists of a cigar shaped, cylindrical balloon attached to a catheter. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is inflated to a size that is consistent with the original diameter of the artery prior to developing occlusive disease. When the balloon is inflated, the plaque is broken. Cleavage planes form within the plaque, permitting the plaque to expand in diameter with the expanding balloon. Frequently, a segment of the plaque is more resistant to dilatation than the remainder of the plaque. When this occurs, greater pressure pumped into the balloon results in full dilatation of the balloon to its intended size. The balloon is deflated and removed and the artery segment is reexamined. The process of balloon angioplasty is one of uncontrolled plaque disruption. The lumen of the blood vessel at the site of treatment is usually somewhat larger, but not always and not reliably.

Some of the cleavage planes created by fracture of the plaque with balloon angioplasty form dissection. A dissection occurs when a portion of the plaque is lifted away from the artery and is not fully adherent and may be mobile or loose. The plaque that has been disrupted by dissection protrudes into the flowstream. If the plaque lifts completely in the direction of blood flow, it may impede flow or cause acute occlusion of the blood vessel. There is evidence that dissection after balloon angioplasty must be treated to prevent occlusion and to resolve residual stenosis. There is also evidence that in some circumstances, it is better to place a metal retaining structure, such as stent to hold open the artery after angioplasty and force the dissected material back against the wall of the blood vessel to create an adequate lumen for blood flow.

Therefore, the clinical management of dissection after balloon angioplasty is currently performed primarily with stents. As illustrated in FIG. 24A, a stent is a tube having a diameter that is sized to the artery. A stent is placed into the artery at the location of a dissection to force the dissection flap against the inner wall of the blood vessel. Stents are usually made of metal alloys. They have varying degrees of flexibility, visibility, and different placement techniques. Stents are placed in every vascular bed in the body. The development of stents has significantly changed the approach to minimally invasive treatment of vascular disease, making it safer and in many cases more durable. The incidence of acute occlusion after balloon angioplasty has decreased significantly with stents.

However, stents have significant disadvantages and much research and development is being done to address these issues. Stents induce repeat narrowing of the treated blood vessel (recurrent stenosis). Recurrent stenosis is the "Achilles heel" of stenting. Depending on the location and the size of the artery, in-growth of intimal hyperplastic tissue from the vessel wall in between struts or through openings in the stent may occur and cause failure of the vascular reconstruction by narrowing or occlusion of the stent. This may occur any time after stent placement. In many cases, the stent itself seems to incite local vessel wall reaction that causes stenosis, even in the segment of the stent that was placed over artery segments that were not particularly narrowed or diseased during the original stent procedure. This reaction of the blood vessel to the presence of the stent is likely due to the scaffolding effect of the stent. This reaction of recurrent stenosis or tissue in growth of the blood vessel is in response to the stent. This activity shows that the extensive use of metal and vessel coverage in the artery as happens with stenting is contributing to the narrowing. The recurrent stenosis is a problem because it causes failure of the stent and there is no effective treatment. Existing treatment methods that have been used for this problem include; repeat angioplasty, cutting balloon angioplasty, cryoplasty, atherectomy, and even repeat stenting. None of these methods have a high degree of long-term success.

Stents may also fracture due to material stress. Stent fracture may occur with chronic material stress and is associated with the development of recurrent stenosis at the site of stent fracture. This is a relatively new finding and it may require specialized stent designs for each application in each vascular bed. Structural integrity of stents remains a current issue for their use. Arteries that are particularly mobile, such as the lower extremity arteries and the carotid arteries, are of particular concern. The integrity of the entire stent is tested any time the vessel bends or is compressed anywhere along the stented segment. One reason why stent fractures may occur is because a longer segment of the artery has been treated than is necessary. The scaffolding effect of the stent affects the overall mechanical behavior of the artery, making the artery less flexible. Available stenting materials have limited bending cycles and are prone to failure at repeated high frequency bending sites.

Many artery segments are stented even when they do not require it, thereby exacerbating the disadvantages of stents. There are several reasons for this. Many cases require more than one stent to be placed and often several are needed. Much of the stent length is often placed over artery segments that do not need stenting and are merely adjoining an area of dissection or disease. Stents that are adjusted to the precise length of the lesion are not available. When one attempts to place multiple stents and in the segments most in need of stenting, the cost is prohibitive since installation and material is required per stent. The time it takes to do this also adds to the cost and risk of the procedure. The more length of artery that receives a stent that it does not need, the more stiffness is conferred to the artery, and the more scaffolding affect occurs. This may also help to incite the arterial reaction to the stent that causes recurrent stenosis.

SUMMARY OF INVENTION

In accordance with the present invention, a device (and related method of deployment) for treating atherosclerotic occlusive disease comprises a thin, annular band of durable, flexible material (a "plaque tack") having a plurality of barbs or anchoring elements on its outer annular periphery, which is installed intravascularly in one or more specific positions of a plaque accumulation site. The plaque tack is dimensioned and designed to be applied with a spring force against the plaque to press and hold it against the blood vessel walls. The barbs or anchoring elements are embedded into or at least emplaced in physical contact against the plaque by the spring force so that the plaque tack is retained securely in position from being dislodged. The plaque tack is generally used after a balloon angioplasty procedure to reopen the vessel lumen for desired blood flow. The annular band of the plaque tack has a width in the axial (length) direction of the vessel walls that is about equal to or less than its diameter, in order to minimize the emplacement of foreign scaffolding structure in the blood vessel. One or more tacks are applied only in positions along the length of a plaque accumulation site where specific holding forces are needed to stabilize the site and/or hold pieces of plaque out of the way of blood flow. The barbs or anchor points of the tack(s) may be pressed with an expansion force into the plaque and/or vessel walls by a post-installation balloon expansion procedure.

In the present invention, the plaque tack device is designed as a minimally invasive approach to tacking loose or dissected atherosclerotic plaque to the wall of the artery, as illustrated in FIG. 24B. It may be used to treat either de novo atherosclerotic lesions or the inadequate results of balloon angioplasty. It is designed to maintain adequate lumen in a treated artery without the inherent disadvantages of vascular stents. The device may also be used to administer medications, fluid, or other treatment ("eluting") agents into the atherosclerotic plaque or the wall of the blood vessel or into the bloodstream.

The plaque tack and installation procedure may be designed in a number of ways that share a common methodology of utilizing an expansion force of the delivery mechanism (such as balloon expansion) and/or the spring force of a compressible annular band to enable the tack to be moved into position in the blood vessel, then released, unfolded or unplied to expand to its full diametral size within the blood vessel walls.

In a preferred embodiment, the tack device comprises a thin, annular band of durable, flexible material having a plurality of barbs or anchoring points on its outer annular periphery, said annular band being dimensioned and designed to be applied with an expansion force against the plaque to press and hold the plaque at an applied site of said band against the blood vessel walls. Besides stabilizing the emplacement of the tack, the barbs play a role in tacking the plaque to the blood vessel wall. The annular band has a length in the axial direction of the blood vessel walls that is about equal to or less than its diameter when expanded. In a ring or ribbon-shaped form, the annular band can have a ratio of length to diameter as low as 1/100. The plaque tack device can also have a structure for carrying medication such that it elutes a biologically active agent to the plaque to inhibit growth and/or for treating the blood vessel wall.

For all embodiments an important parameter characterizing design of a plaque tack is the ratio: Vessel Coverage Area (C) to Total Vessel Surface area (TVS), where C/TVS is less than or equal to about 60%. This equation can be applied to one tack device or when several spaced-apart tack devices are placed across the length of a blood vessel treatment area.

In another preferred embodiment, a tack device is formed with concentric side rings or mesh bands connected by longitudinal bridge members. As adapted from a measure of Relative Metal Surface Area (RMS) compared to the number of longitudinal segments in the device structure, an equation for Effective Metallic Interface (EMI) may be used to compare this embodiment of the tack device to a typical stent, as follows:

$$EMI = \frac{(1+n^2)C}{\sum_{s=1}^{x}(lw)_s}$$

where x is the number of sections of metal, l is an individual metal section length, w is an individual metal section width, C is the vessel coverage area underneath the device (lumen surface), and n is the number of bridge members longitudinally connected between circumferentially oriented segments. The summation found in the denominator can be interpreted as the total metal surface area. The preferred embodiment of the tack device has an EMI≦10, whereas the EMI of a typical stent would be several times greater.

The present invention also encompasses the method of using the tack device to treat any plaque dissection in the blood vessel after balloon angioplasty by installing it with an expansion force against the plaque to hold it against the blood vessel walls. A most preferred method encompasses one wherein drug eluting balloon angioplasty is first performed, and if there is any damage, disruption, dissection, or irregularity to the blood vessel caused by the balloon angioplasty, one or more tack devices may be used to tack down the damaged, disrupted, dissected, or irregular blood vessel surface, so as to avoid the need to install a stent and thereby maintain a 'stent-free' environment.

Other objects, features, and advantages of the present invention will be explained in the following detailed description of the invention having reference to the appended drawings.

BRIEF DESCRIPTION OF DRAWINGS

FIGS. 1A and 1B are schematic diagrams of a first embodiment in ribbon form for the plaque tack device of the present invention.

FIG. 2 is a side view of the first embodiment of the ribbon tack of FIG. 1B in its annular shape after deployment.

FIG. 3 is a plan view of the ribbon tack of FIG. 1B in its annular shape after deployment.

DETAILED DESCRIPTION OF INVENTION

Figure 4A:
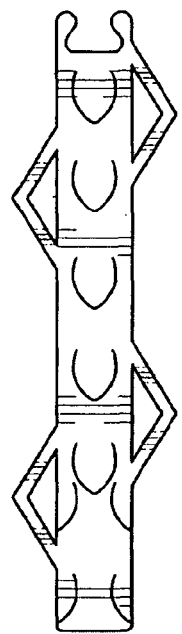
FIG. 4 is an alternative version of the ribbon tack of FIG. 1B having stabilizing wings.

In the following detailed description of the invention, certain preferred embodiments are illustrated providing certain specific details of their implementation. However, it will be recognized by one skilled in the art that many other variations and modifications may be made given the disclosed principles of the invention. Reference for the description is made to the accompanying drawings, wherein like reference numerals refer to similar parts throughout the several views.

Figure 24A:
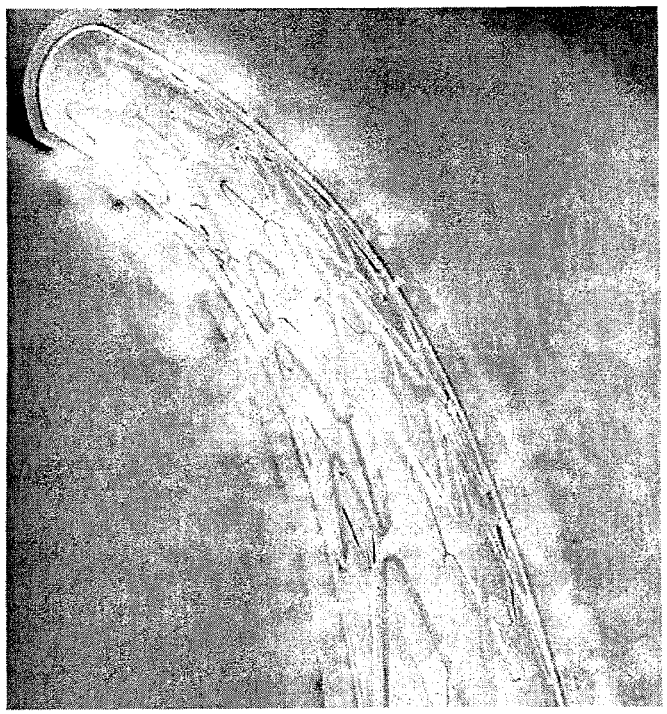
FIG. 24A illustrates the use of a stent installed after angioplasty as conventionally practiced in the prior art.
Figure 24B:
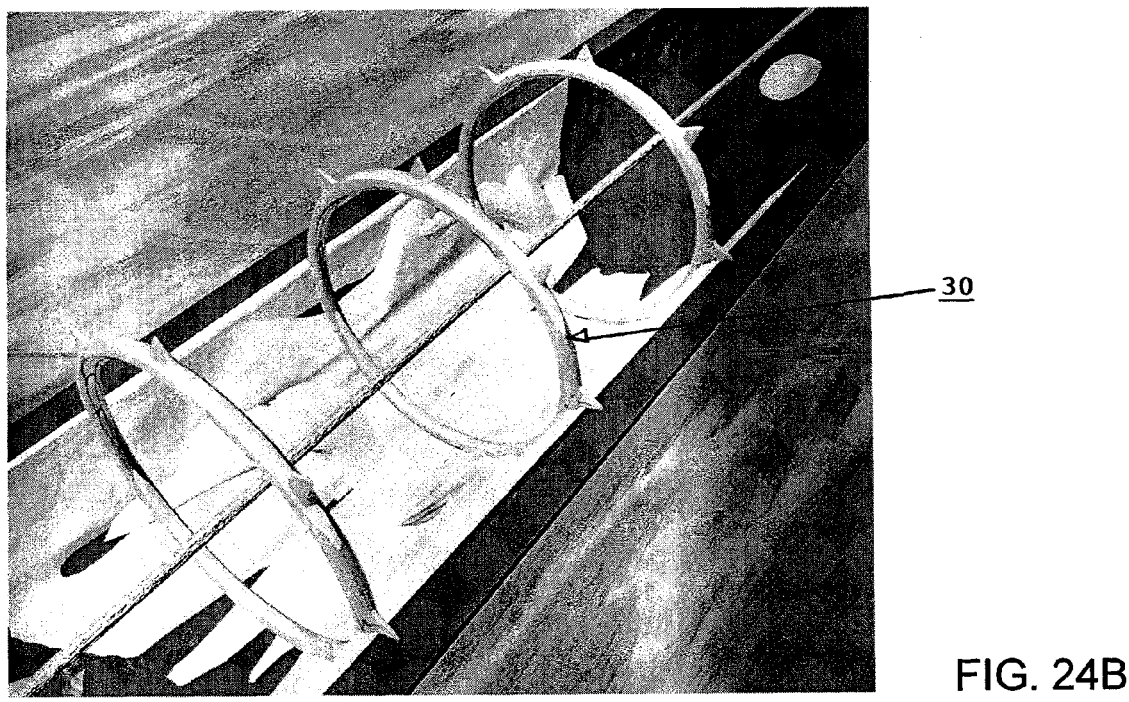
FIG. 24B illustrates the use of the plaque tack installed after angioplasty demonstrating its advantages over the prior art.

As illustrated in FIG. 24B, the plaque tack device in the present invention generally comprises a thin, annular band of durable, flexible material having a plurality of barbs or anchoring elements on its outer annular periphery. The plaque tack is dimensioned diametrally and is designed to be applied with a spring force against the plaque to press and hold it against the blood vessel walls. The barbs or anchoring elements are embedded into or at least emplaced in physical contact against the plaque by the spring force of the plaque tack. The plaque tack extends over only a small area in the axial direction of the vessel walls, in order to minimize the amount of foreign structure placed in the blood vessel. One or more tacks are applied only in positions along the length of a plaque accumulation site where specific holding forces are needed to stabilize the site and/or hold pieces of plaque out of the way of blood flow.

The plaque tack and installation procedure may be designed in a number of ways that share a common methodology of utilizing the spring force of a spring-like annular band to enable the tack to be compressed, folded, or plied to take up a small-diameter volume so that it can be moved into position in the blood vessel on a sheath or catheter, then released, unfolded or unplied to expand to its full-diametral size within the blood vessel walls.

In the following description, five general embodiments of the plaque tack device and how to deliver it are explained in detail, referred to as: (1) ribbon tack; (2) folding ring tack; (3) flexible ring tack; (4) spiral coil tack; and (5) metallic mesh tack. All these embodiments are delivered into the blood vessel from endovascular insertion. The delivery device for each involves a delivery apparatus that has some features of a vascular sheath. The delivery device for each is different and has features that are specifically designed to deliver the specific tack Referring to FIGS. 1A and 1B, a first preferred embodiment of the plaque tack device is shown in two versions of a ribbon tack, each having a linear, flat shape like a ribbon. The version in FIG. 1A has a base end 31, rows 33 of cutout tongues or apertured portions that open out as pointed barbs or anchors, and a retainer end 35. The version in FIG. 1B has a base end 32, single row 34 of cutout portions that open out as pointed barbs or anchors, and a retainer end 35. Each version may be made of a material such as a corrosion-resistant metal, polymer, composite or other durable, flexible material. A preferred material is a metal having "shape-memory" (such as Nitinol) which allows it to be formed initially with an annular shape prior to forming in a linear shape, then resume the annular shape when exposed for a length of time at internal body temperature. When the strip is deployed in the blood vessel, it is curved into an annular shape. FIG. 2 shows the view of the strip of material in FIG. 1B after it is curved into its preferred shape of deployment in the blood vessel, leaving a large inner, open area 36 for blood flow through it. The barbs are shown opened to outwardly pointing angles 37 due to bending forces so that they point toward the wall or surface of the blood vessel.

In a typical configuration, the ribbon tack may have a width of about 0.1 to 5 mm, a diameter (when curved in annular shape) of about 1 to 10 mm, a length (when extended linearly) of about 3 to 30 mm, and a barb height from 0.01 to 5 mm. In general, the annular band of the plaque tack has a width in the axial direction of the vessel walls that is about equal to or less than its diameter, in order to minimize the amount of foreign structure to be emplaced in the blood vessel. For tack designs in a ring or ribbon shape, the width/diameter ratio can be in the range of $1/10$ to $1/100$.

Figure 4B:
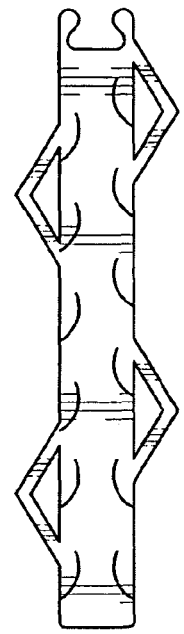
Figure 8:
FIG. 8 is a photo image of the ribbon tack of FIG. 1B showing the tongues or cutout portions protruding at an angle from the metal strip when the tack is bent into an annular shape.
Figure 9:
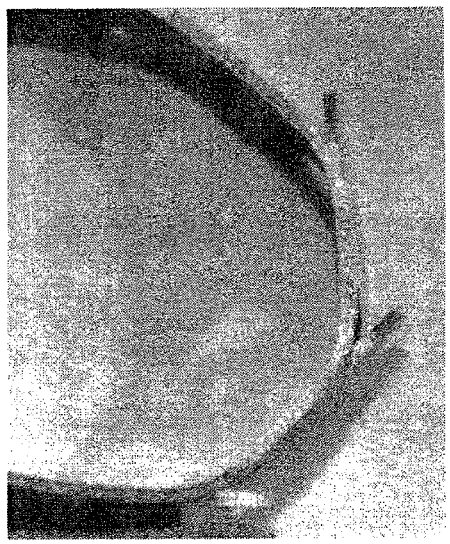
FIG. 9 is a close-up image of the anchor points of the ribbon tack of FIG. 1B.
Figure 10:
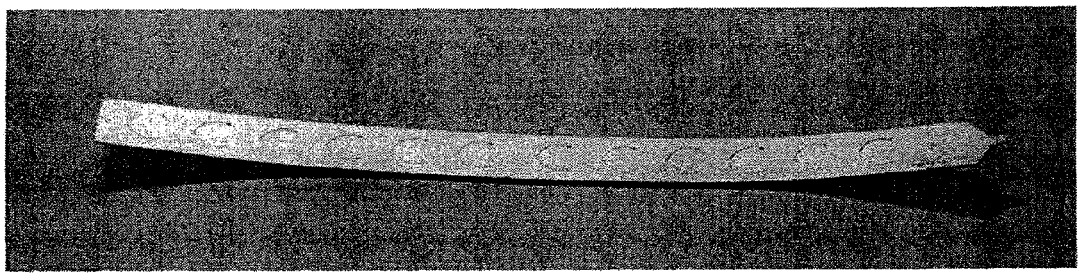
FIG. 10 is a photo image of the ribbon tack of FIG. 1B prior to installation.

FIG. 3 is a schematic diagram showing a top view of the ribbon tack bent into its annular shape. FIG. 4 shows an alternative version of the ribbon tack having stabilizing wings provided along its side edges for added lateral stability when deployed in the blood vessel. FIG. 8 shows an overhead photo image of the ribbon tack with anchors protruding at an outward angle. FIG. 9 is a close-up image of the anchors of the annular strip. FIG. 10 is an overhead image of the metal strip extended linearly when at rest.

Figures 11, 12:
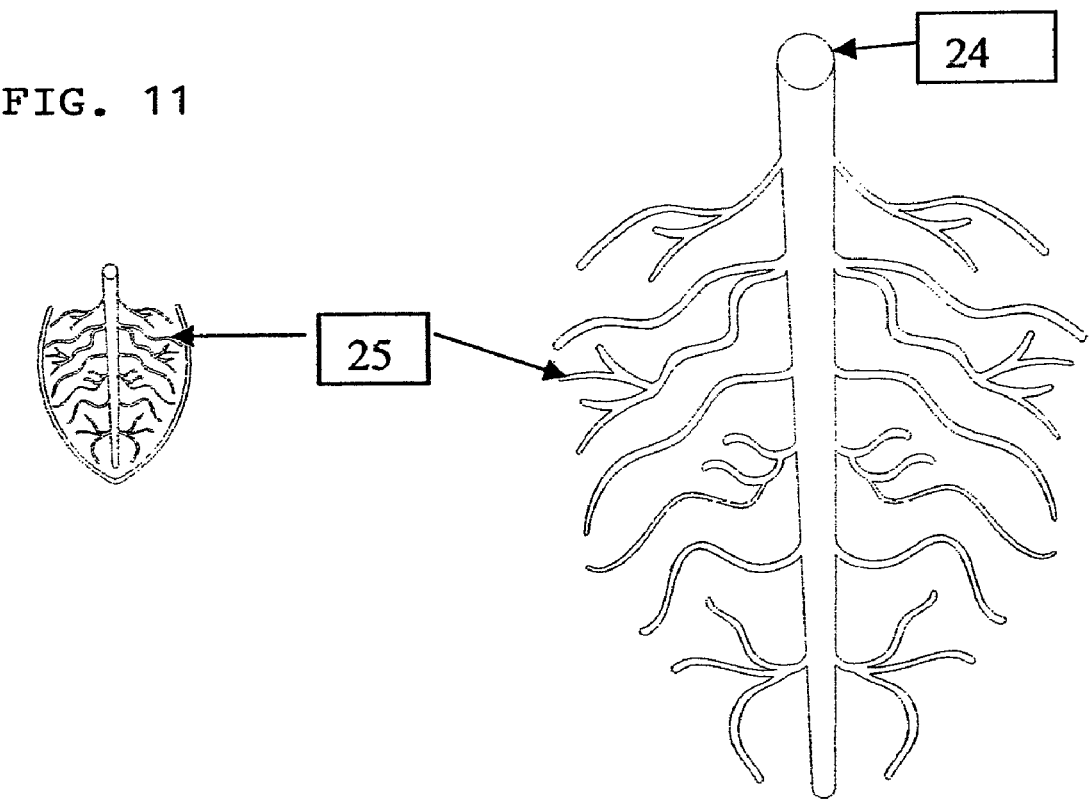
FIG. 11 illustrates a pattern of capillaries formed on the tongues of the ribbon tack of FIG. 1B for delivering plaque-growth retarding material into the plaque.
FIG. 12 is a close-up view of the capillaries formed on the tongues of the ribbon tack in FIG. 11.

FIG. 11 illustrates a pattern of capillaries 25 that may be formed by etching the surfaces of the tongues or cutout portions for delivering plaque-growth retarding material or other treatment agent where the tack is installed at the plaque accumulation site. FIG. 12 illustrates how the pattern of capillaries 25 is supplied with plaque-retarding or treatment material through a supply conduit 24. The material may be either resident within the channels prior to insertion of the tack or transferred from a reservoir on the inside of the annulus, through a hole to the outside of the component on the surface, into the anchored object, and into the tissue wall, enabling delivery of a treatment or such that enables additional preventative measures for retaining optimal blood flow. The forces that enable the transfer of the material from the inside of the annulus through the tree branches might be either capillary force or a combination of capillary and hydraulic pressure. Capillary action, capillarity, capillary motion, or wicking is the ability of a substance to draw another substance into it. The standard reference is to a tube in plants but can be seen readily with porous paper. It occurs when the adhesive intermolecular forces between the liquid and a substance are stronger than the cohesive intermolecular forces inside the liquid. The effect causes a concave meniscus to form where the substance is touching a vertical surface.

The array of barbs or anchor points is used for linking the annular band of the tack with the plaque mass or blood vessel wall. The barb is made of a sufficiently rigid material to sustain a locking relationship with the blood vessel tissue and/or to pierce the plaque and maintain a locking relationship therewith. The barb is comprised of a head disposed on a support body. Preferably, the head and support body are integral with each other and are constructed as a single piece. The barb may project at an angle of 90 degrees to the tangent of the annular band, or an acute angle may also be used.

Figure 13:
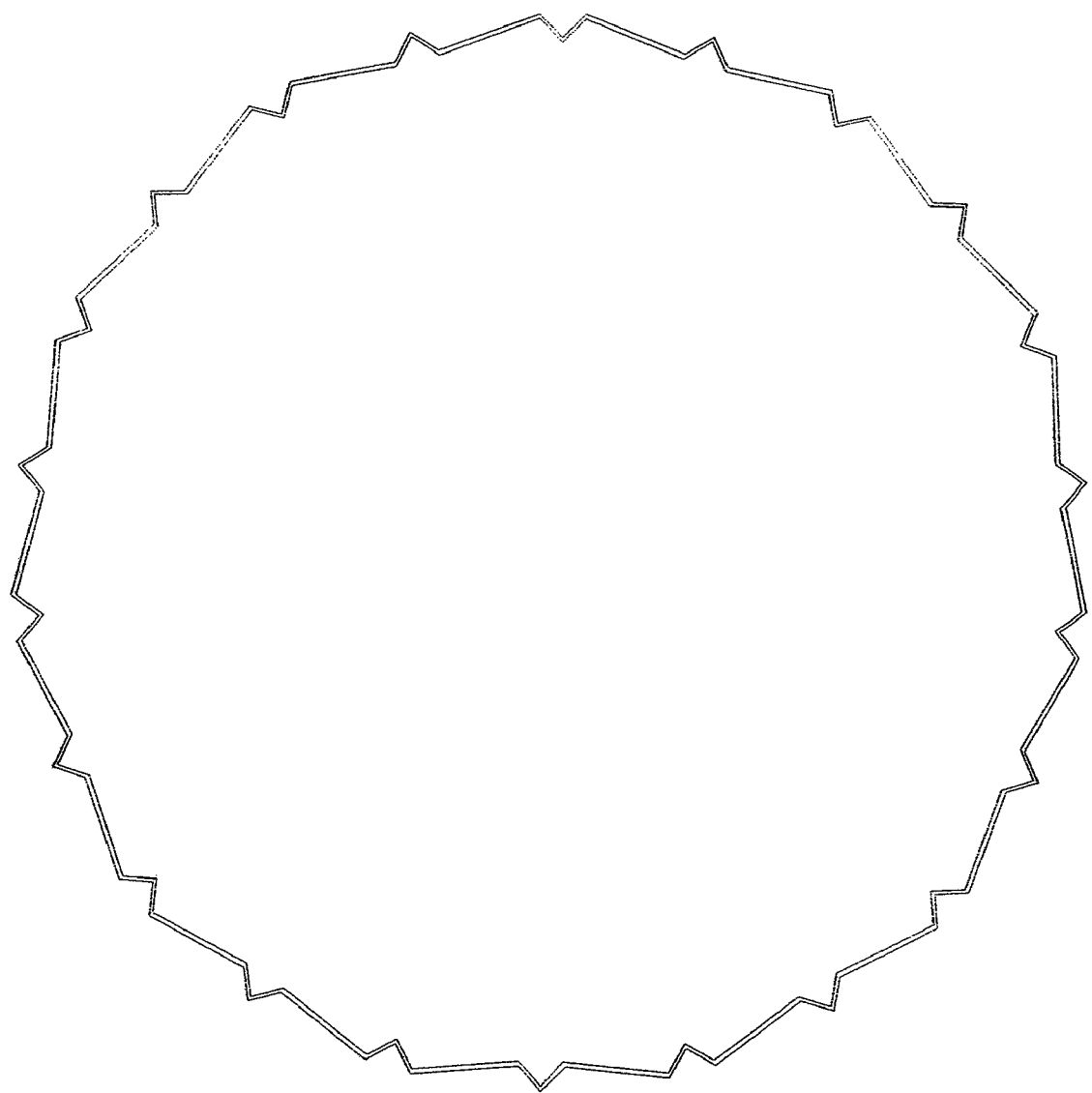
FIG. 13 is a schematic diagram of a second embodiment of a folding ring tack having inner V-shaped segments for folding and outer inverted-V-shaped points for anchoring.

Referring to FIG. 13, a second preferred embodiment of the plaque tack device is formed as a folding ring tack having inner V-shaped segments for folding alternating with outer inverted-V-shaped points. The V-shaped segments allow the ring to be radially folded to a small-diameter volume for carriage on a deployment tube on the end of the sheath. At the desired position in the blood vessel, the compressed ring tack is released from the deployment tube so that the ring springs out to its full diametral shape and the outward points act as barb or anchor points embedded into or pressed against the plaque. The folding ring tack is preferably made of metal wire material. Other options for the shape of the anchors on the outer surface may be used.

Figure 5:
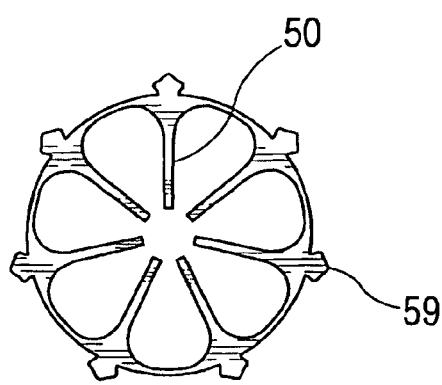
FIG. 5 is a schematic diagram of a third embodiment of flexing star tack having outward triangular anchor points and inward radial fingers.

Referring to FIG. 5, a third preferred embodiment of the plaque tack device is formed as a flexible ring tack having a pliable or hinged structure and formed with an array of radially extending points 59 on an outer side of the ring, and an array of inner radial fingers 50. The array of inner radial fingers are used to displace the points to lie horizontally flat in one axial direction when the fingers and pushed in the opposite axial direction. With the barbs or points displaced to lie horizontally flat, the flexible ring tack can be loaded on a catheter delivery tube and held down by a cover. The fingers are then removed so that they are not present to obscure the blood vessel when the tack is installed. At the desired position, the retainer cover is displaced to release the ring tack which springs up to extend its points radially outwardly for embedding into the plaque. The body of the annular ring may have differing degrees of thickness and different designs for the fingers in the central area, such as the raised triangular anchors 59 and radial fingers 50 shown in FIG. 5.

FIGS. 7A-7D show alternative shapes for the third embodiment of FIG. 5 with a variety of different anchoring designs 72, 73, 78, 80. The fingers 76, 77 for bending the points flat for insertion are included with any of the designs. When the fingers are removed after pre-loading, and the flexible ring tack has been deployed, the inner area 74, 75 within the annular ring 79, 82 is left unobstructed.

Figure 6:
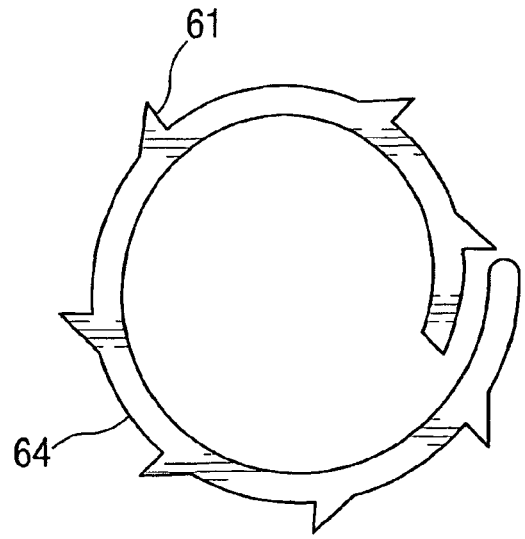
FIG. 6 is a schematic diagram of a fourth embodiment of a spiral coil tack with unjoined ends that can be pulled in opposite directions horizontally to reduce its cross-sectional diameter for insertion in the blood vessel.
Figure 7A:
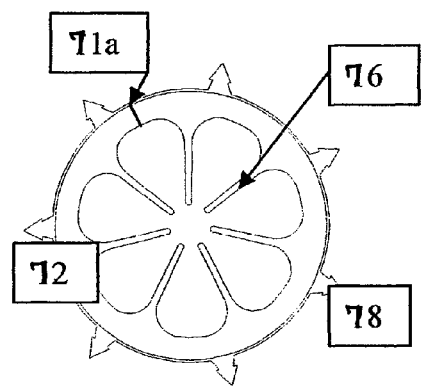
FIGS. 7A-7D show alternative shapes for the flexing star tack of FIG. 5 with a variety of different anchor point designs.
Figure 7B:
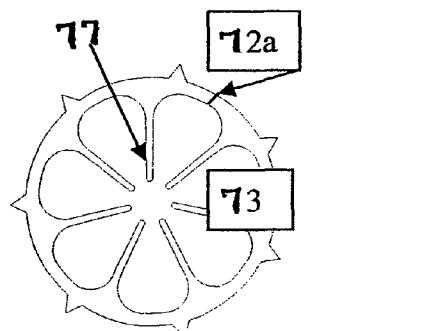
Figure 7C:
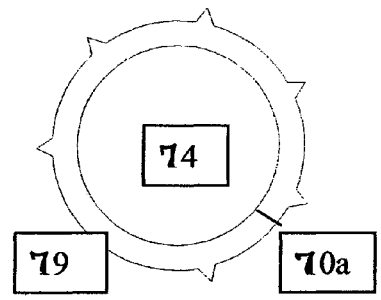
Figure 7D:
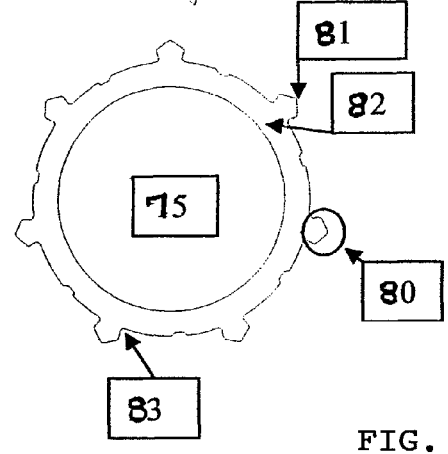

Referring to FIG. 6, a fourth preferred embodiment of the plaque tack device is formed in a coil shape 64 with ends unjoined and with barbs or points 61 on its outer periphery. The ends are pulled longitudinally in opposite directions to flatten the annular band to a spiral shape extending linearly so that it can be carried around or inside the length of a tubular sheath into the blood vessel held in place by a retainer element. At the desired position in the blood vessel, the retainer element is released to allow the tack to expand back to its full-diameter annular shape against the plaque.

Figure 14:
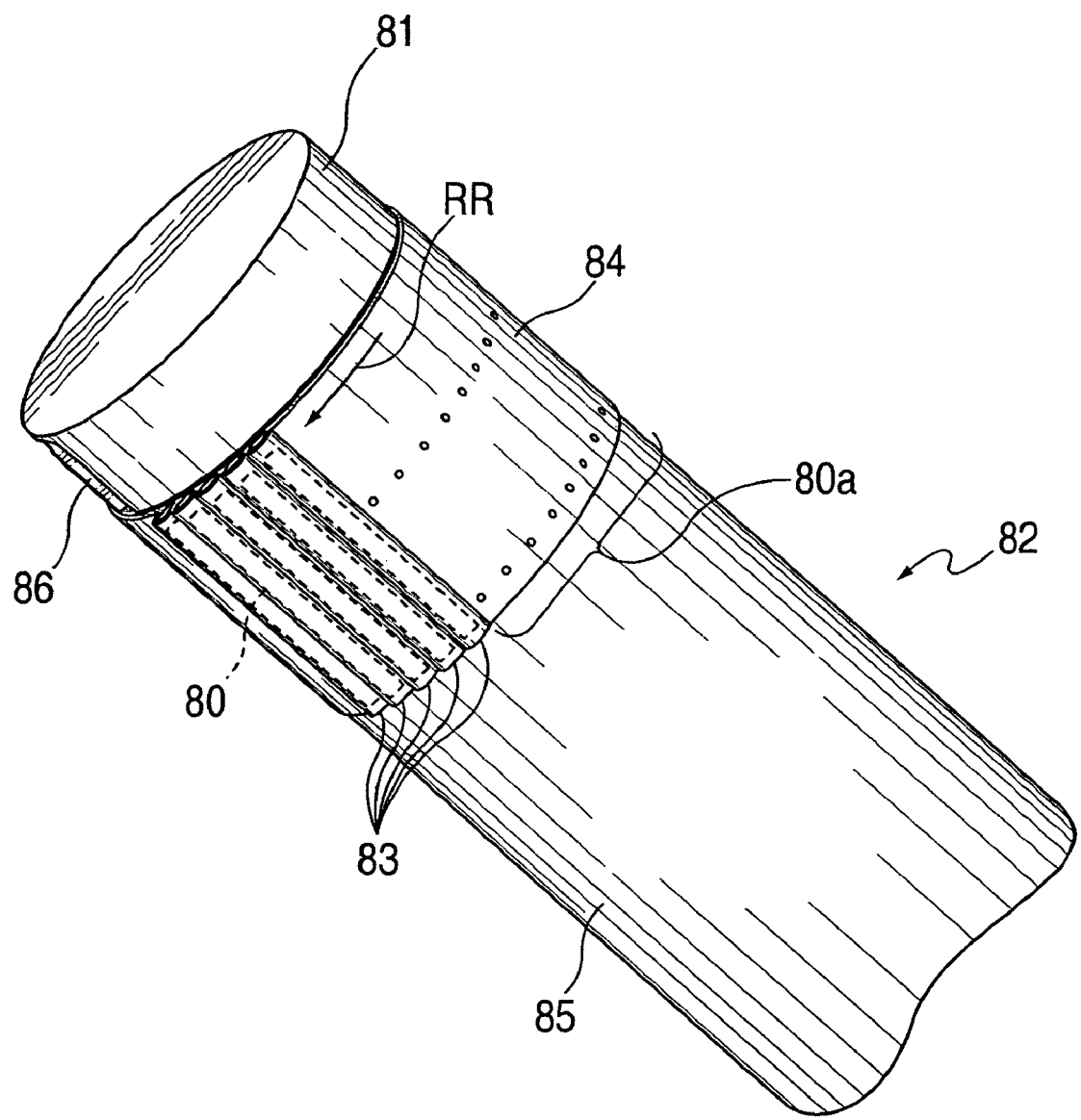
FIG. 14 is a schematic representation of the ribbon tack loaded in multiple units on the delivery head of a catheter tube for insertion into the blood vessel.
Figure 15:
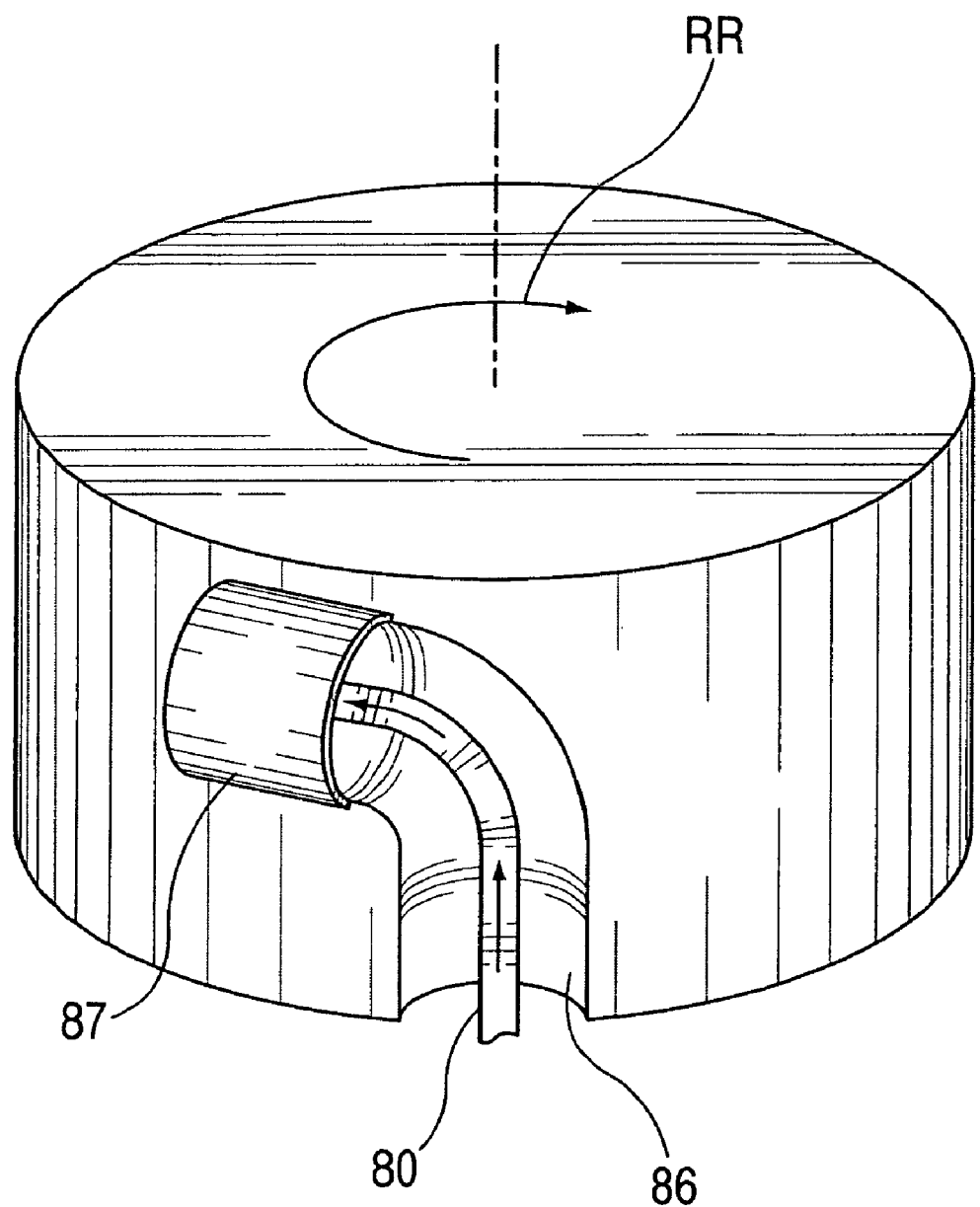
FIG. 15 is a detailed view of the delivery head for the ribbon tacks in FIG. 14.

FIGS. 14 and 15 show a preferred delivery method for the ribbon tack described above. Multiple flat ribbon strips 80 in linear form are arranged in parallel in an array 80a carried on the outer surface of the delivery head 81 of a tubular catheter 82. Each ribbon strip 80 is carried in a respective barrel 83 of a multi-barreled tack magazine 84 which wraps around the catheter, as indicated in FIG. 14. The catheter has an internal pressure chamber 85 which is loaded with saline solution or $CO_2$ gas used to eject a ribbon strip from its barrel as it is moved by rotation of the magazine 84 in the direction RR to bring each ribbon strip in turn to an ejector position (left side of the figure) in alignment with an ejector track 86 formed in the delivery head. Pressurized fluid from the pressure chamber 85 is used to push a mover member that ejects the ribbon strip from its barrel into the ejector track 86. As shown in more detail in FIG. 15, the ejector track 86 leads into a curved outlet tunnel 87 which bends the ribbon strip towards its annular shape as the delivery head rotates. The outlet tunnel 87 curves 90 degrees from the axial direction of the catheter to the radial direction facing toward the vessel walls. This curved tunnel captures the end of the ribbon pushed into the ejector track and causes the middle part of the ribbon strip to bulge outward toward the blood vessel wall where it will lay down perpendicular to the axis of the blood vessel. The delivery head of the catheter rotates as part of the delivery mechanism. As the ribbon is being pushed out of the delivery head under hydraulic or propulsive pressure, the rotation of the delivery head allows the ribbon to be laid down in its annular shape spanning the blood vessel walls.

Figure 16:
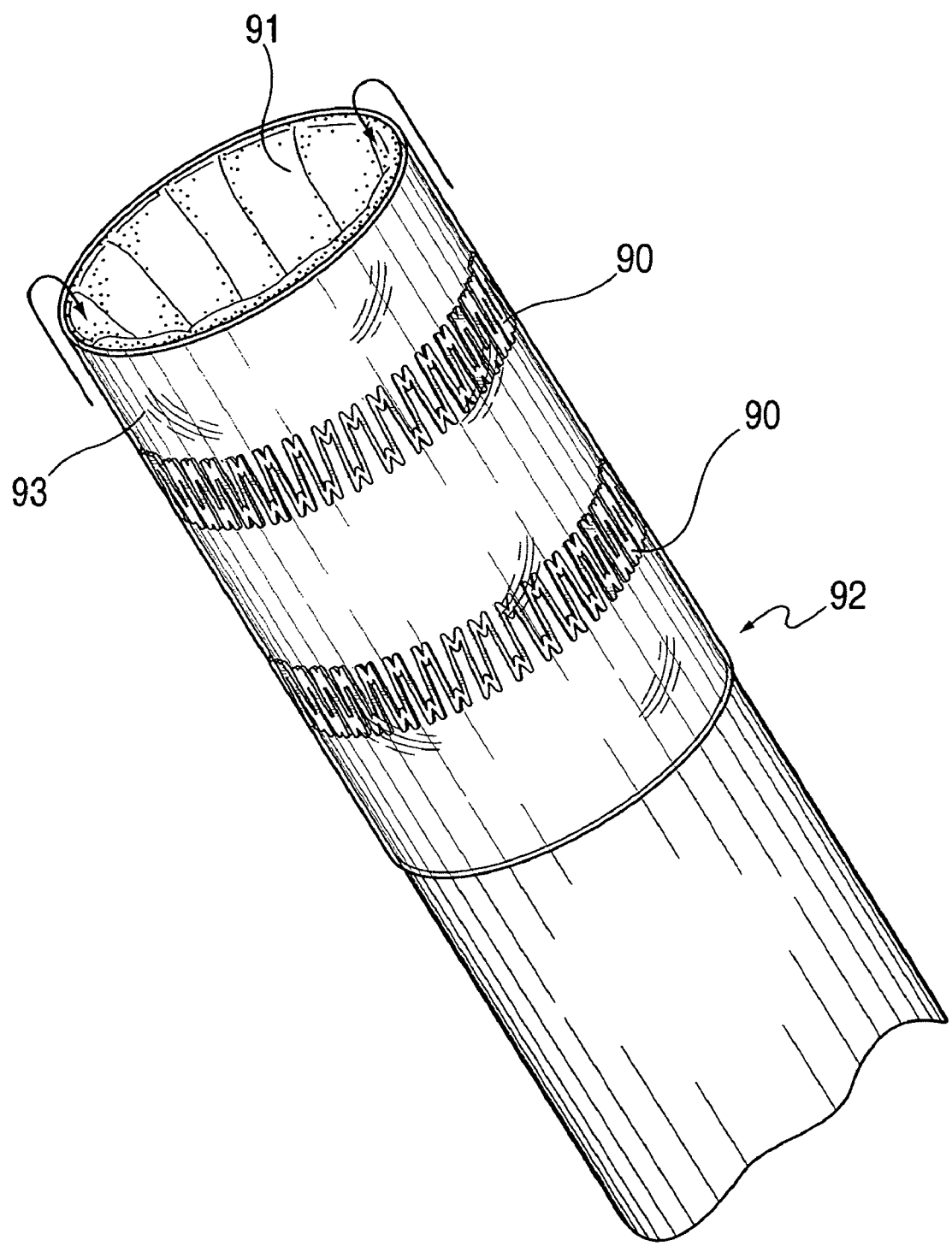
FIG. 16 is a schematic representation of the folding ring tack loaded in multiple units on the delivery head of a catheter tube with a retainer for holding them on the sheath in compressed form.
Figure 17:
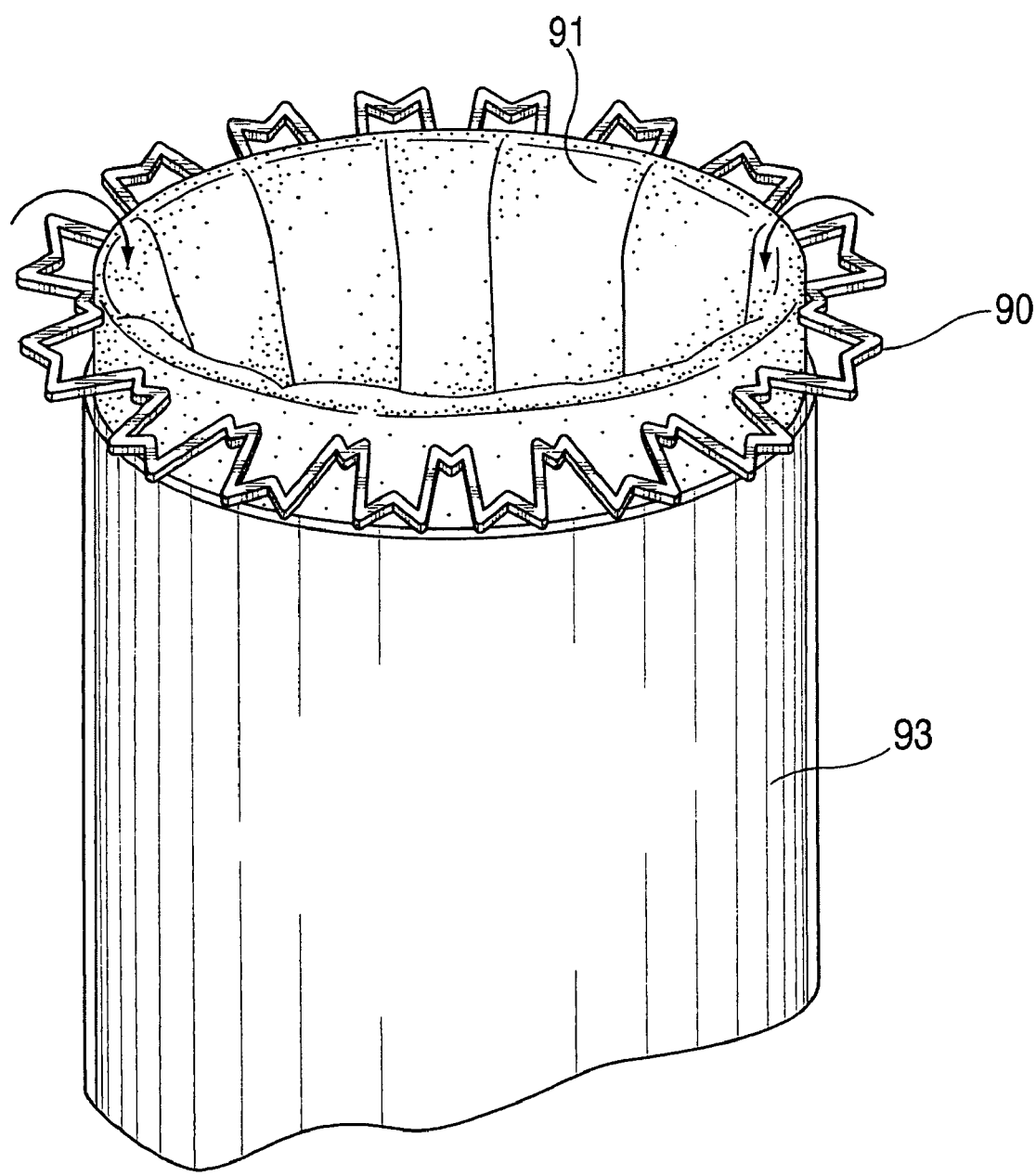
FIG. 17 is a schematic representation showing the folding ring tack partially deployed.
Figure 18:
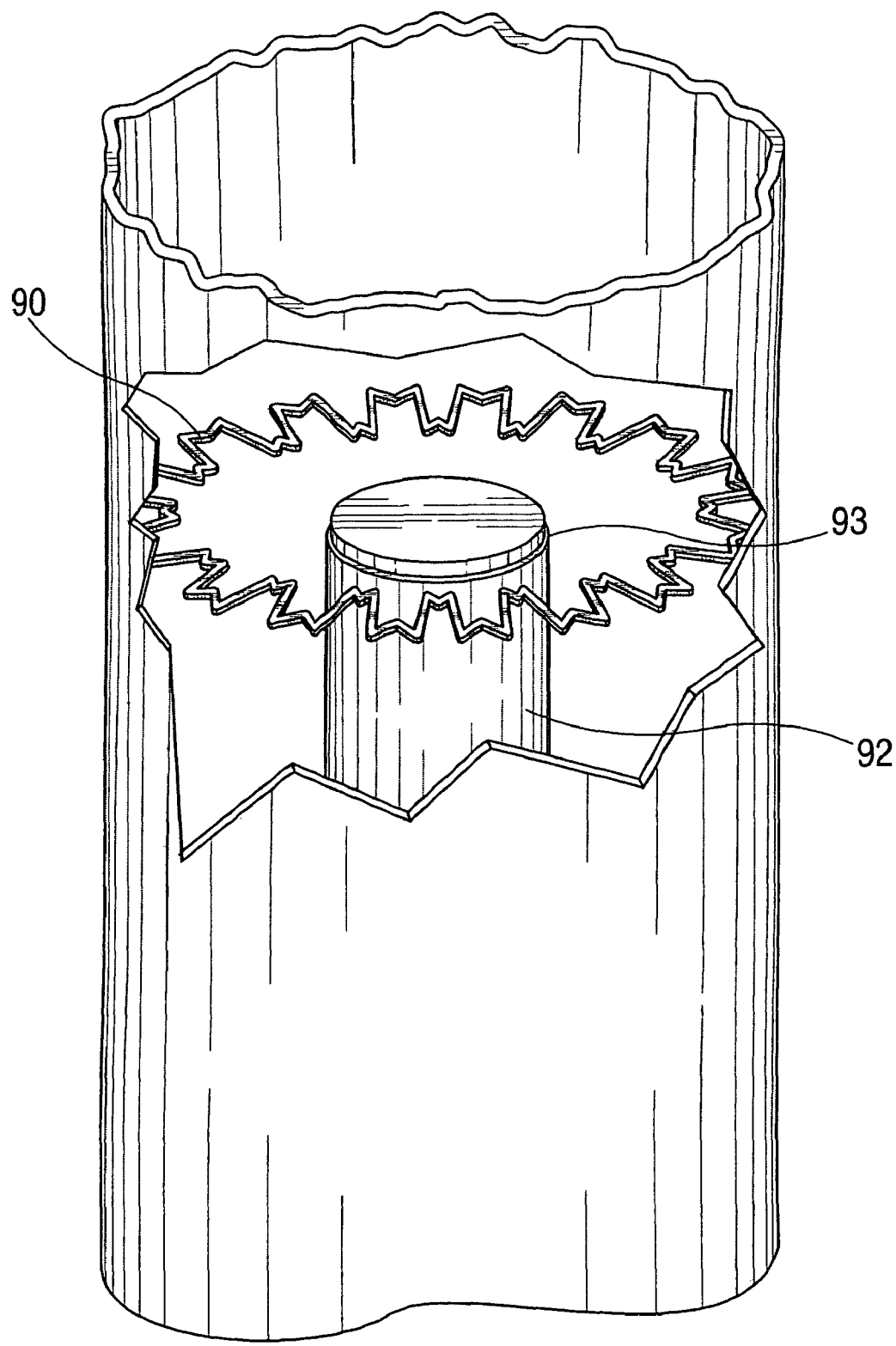
FIG. 18 is a schematic representation showing folding ring tack fully deployed in the blood vessel.

A preferred delivery method for the second described embodiment of the folding ring tack of FIG. 13 is shown in FIGS. 16, 17, and 18. The folding ring tack has an overall circular shape with inner V bends that allow it to be folded in zig-zag fashion to a compressed smaller-volume form for loading onto the delivery end of a catheter tube 92. As shown in FIG. 16, multiple units of the compressed folding ring tacks 90 are arrayed in a series on the surface of the tube. The catheter tube is hollow and lined with a fabric 91 that slides over the outer surface of the tube and is pulled over the end of the tube into its interior (direction of the U-shaped arrows). The fabric is made of a strong, durable material with low friction such as Teflon or Kevlar or like material. Multiple tacks may be loaded onto the surface of the fabric covering the outer surface of the catheter tube. The tacks are held down in their compressed, folded form by a shell or cover 93 that is telescoped over the catheter tube and prevents early deployment of the tacks. The shell may be a transparent plastic sleeve or similar structure having its end set back a small distance from the end of the catheter tube. As the fabric 91 is pulled inside the tube is pulled, the compressed tack 90 is advanced toward the end of the catheter tube. When the tack reaches the end, it is released from the shell 93, and springs back to its original shape of an annular band with outer barbs the embed or are emplaced against the plaque and blood vessel walls. FIG. 17 shows this process in action with the tack half-way deployed. The fabric 91 advancing the tack 90 is being pulled into the center of the hollow delivery tube. FIG. 18 shows the tack in place in the blood vessel after it has been separated from the delivery catheter.

The third preferred embodiment of the flexing ring tack of FIG. 5 may be deployed by a similar method as described above, by loading onto a similar sliding fabric carrier which is pulled over the outer surface of a catheter tube, with a shell sleeved over the tube for retaining the tacks from deployment until each reaches the end of the tube.

Figure 19A:
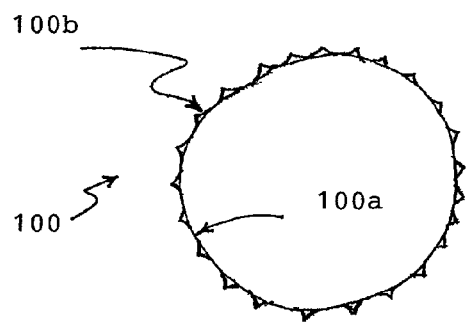
FIG. 19A shows a fifth embodiment of a metallic mesh tack in end view.
Figure 19B:
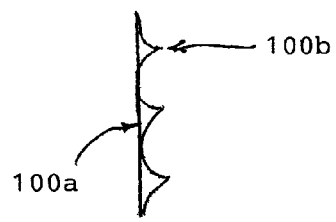
FIG. 19B shows it in side view.
Figure 19C:
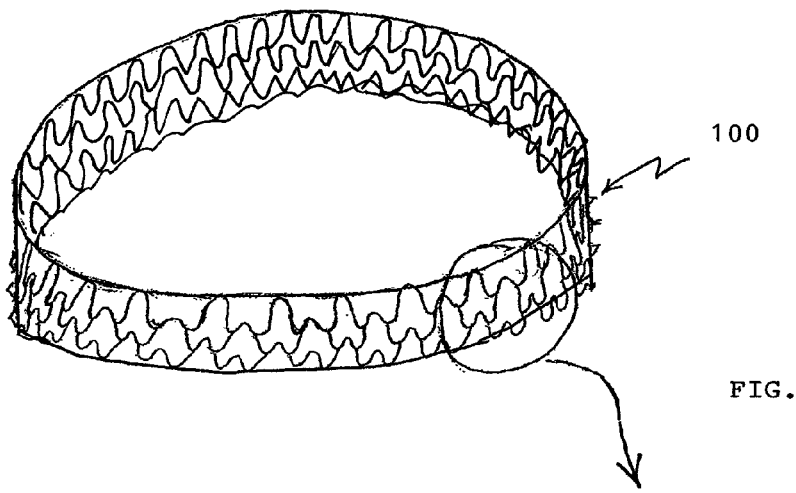
FIG. 19C shows the metallic mesh tack in perspective.
Figure 19D:
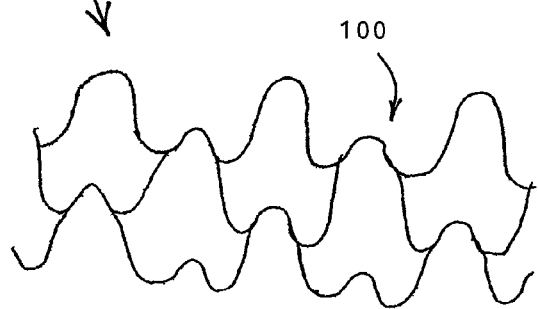
FIG. 19D shows a section of the metallic mesh tack in a detailed view.
Figure 20:
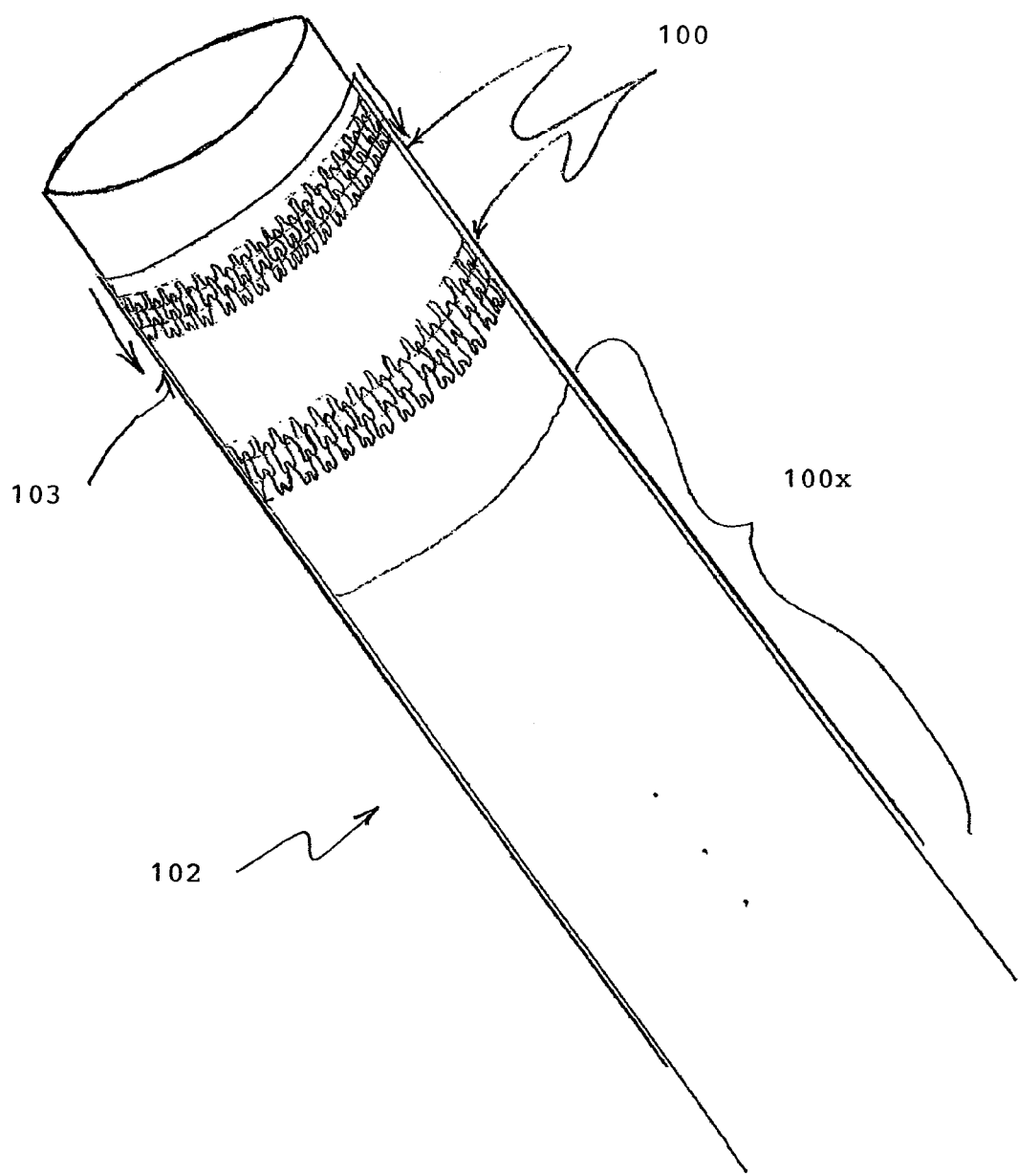
FIG. 20 is a schematic representation showing multiple units of the metallic mesh tack loaded on a catheter delivery tube.
Figure 21:
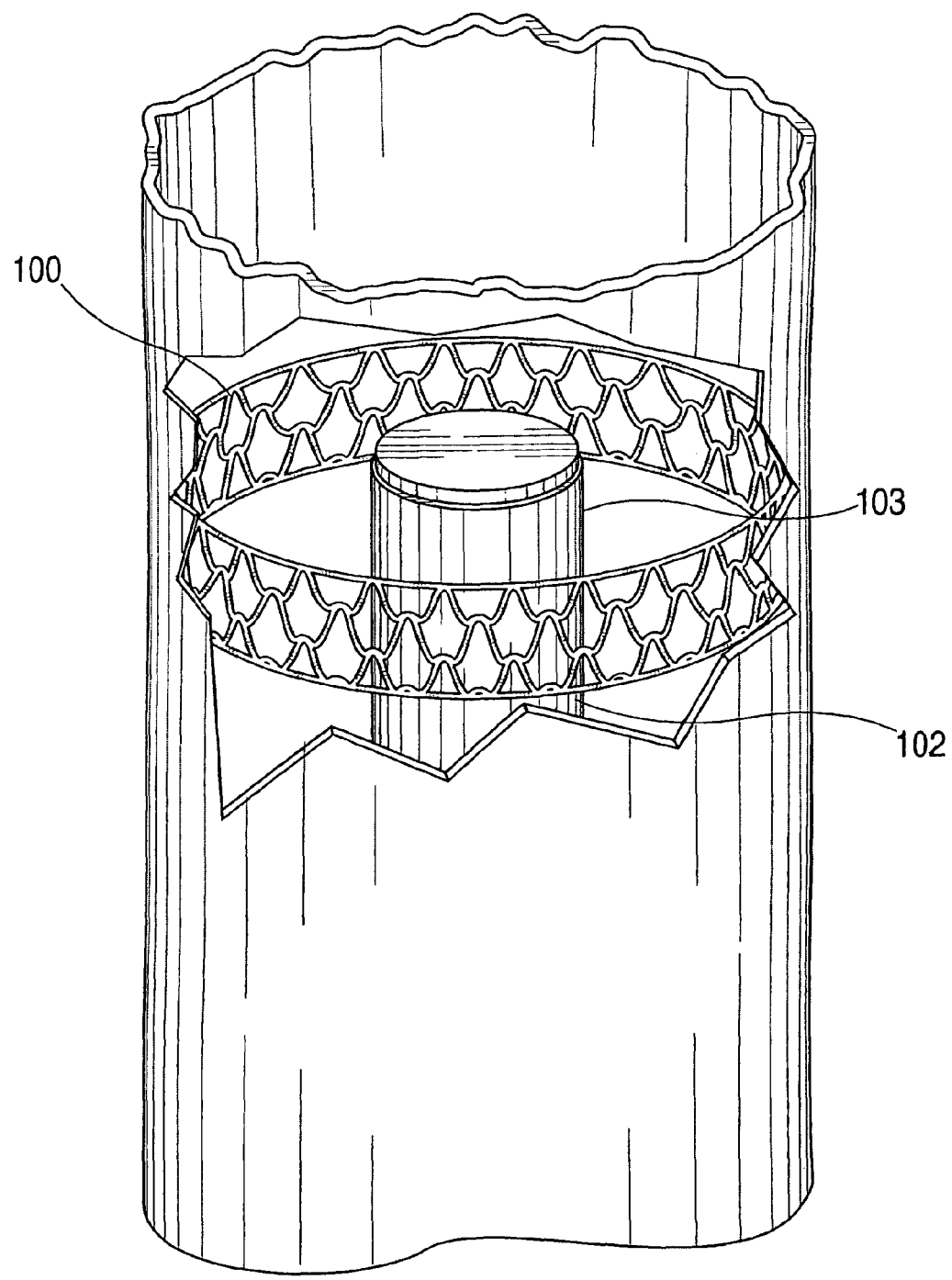
FIG. 21 is a schematic representation showing the metallic mesh tack released from the delivery head and fully expanded in the blood vessel.

A fifth embodiment of the plaque tack in the form of a metallic mesh tack is illustrated in FIGS. 19A-D, and its manner of deployment in FIGS. 20 and 21. In FIG. 19A, the metallic mesh tack is shown in end view having an annular band 100a formed of interleaved mesh, and outer points or barbs 100b. The metallic mesh tack may be laser cut or etched out of a metal tube form or made of thin metal wire which is looped and interleaved in a mesh that is welded, soldered, looped and/or linked together into the desired mesh shape. FIG. 19B shows the metallic mesh tack in side view with barbs projecting from the annular band 100a. The barbs on its outward surface will contact and embed into the wall of the blood vessel. FIG. 19C shows the metallic mesh tack at rest in its fully expanded state in perspective view, and FIG. 19D shows a section of the metallic mesh tack in a detailed view. The mesh pattern is specifically designed so that it can be compressed radially inward to a smaller-volume size for loading on a catheter delivery device to be inserted into the blood vessel.

A preferred method of delivery for the metallic mesh tack is shown in FIG. 20. Multiple mesh tacks 100 are compressed to its smaller-volume size and loaded onto the surface of a catheter delivery tube 102 in an array 100x over a given length of the tube. As in the previously described delivery method, a cover or shell 103 is sleeved over the surface of the tube to hold the tacks in their compressed state and prevent early deployment of the tacks. As the cover 103 is withdrawn down the length of the tube, each mesh tack in turn is released and expands to its full-volume size. FIG. 21 shows the mesh tack 100 expanded and deployed in the blood vessel.

Figure 22:
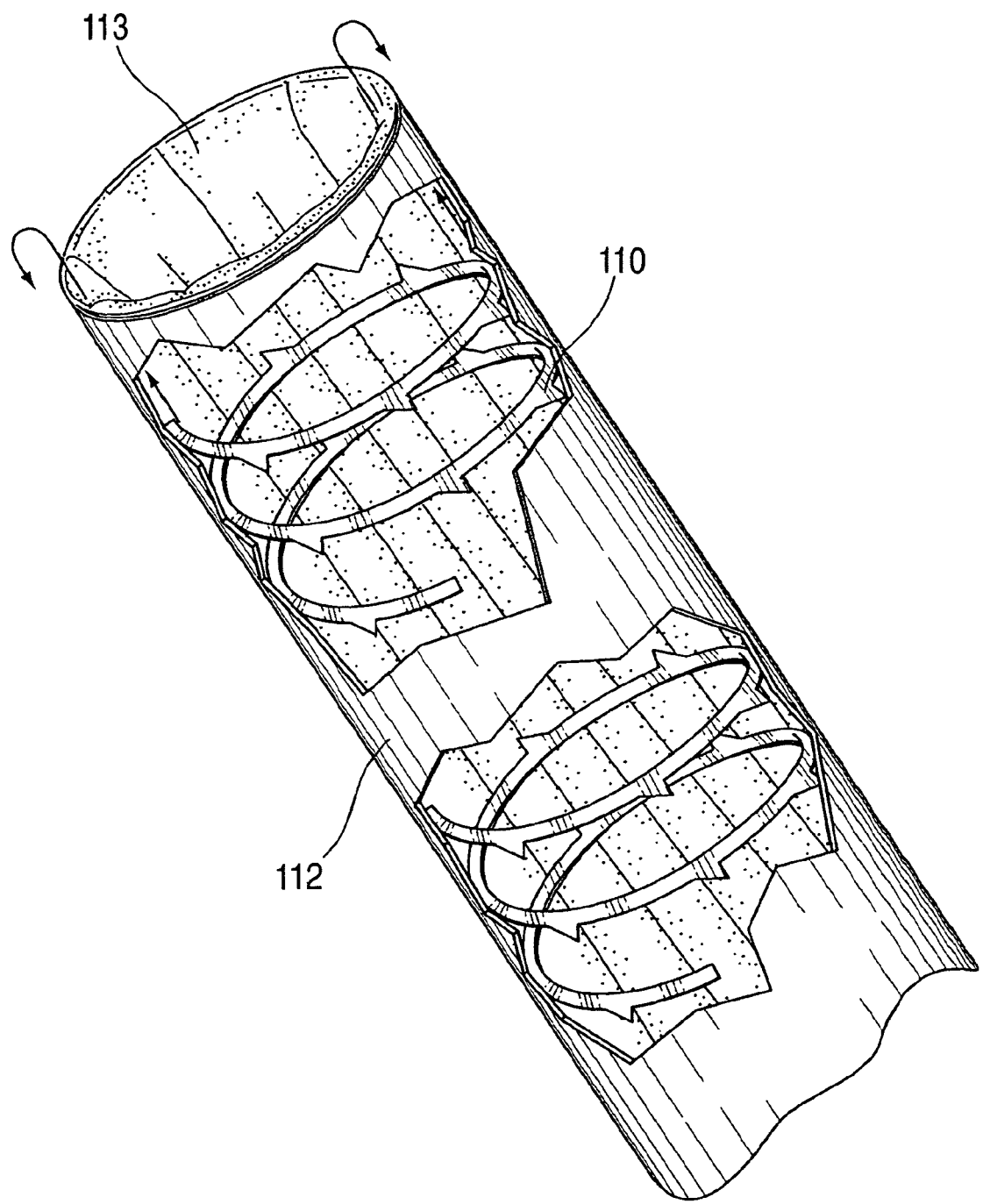
FIG. 22 is a schematic representation the spiral coil tack loaded in multiple units on the delivery head of a sheath and held down by a retainer cover.
Figure 23:
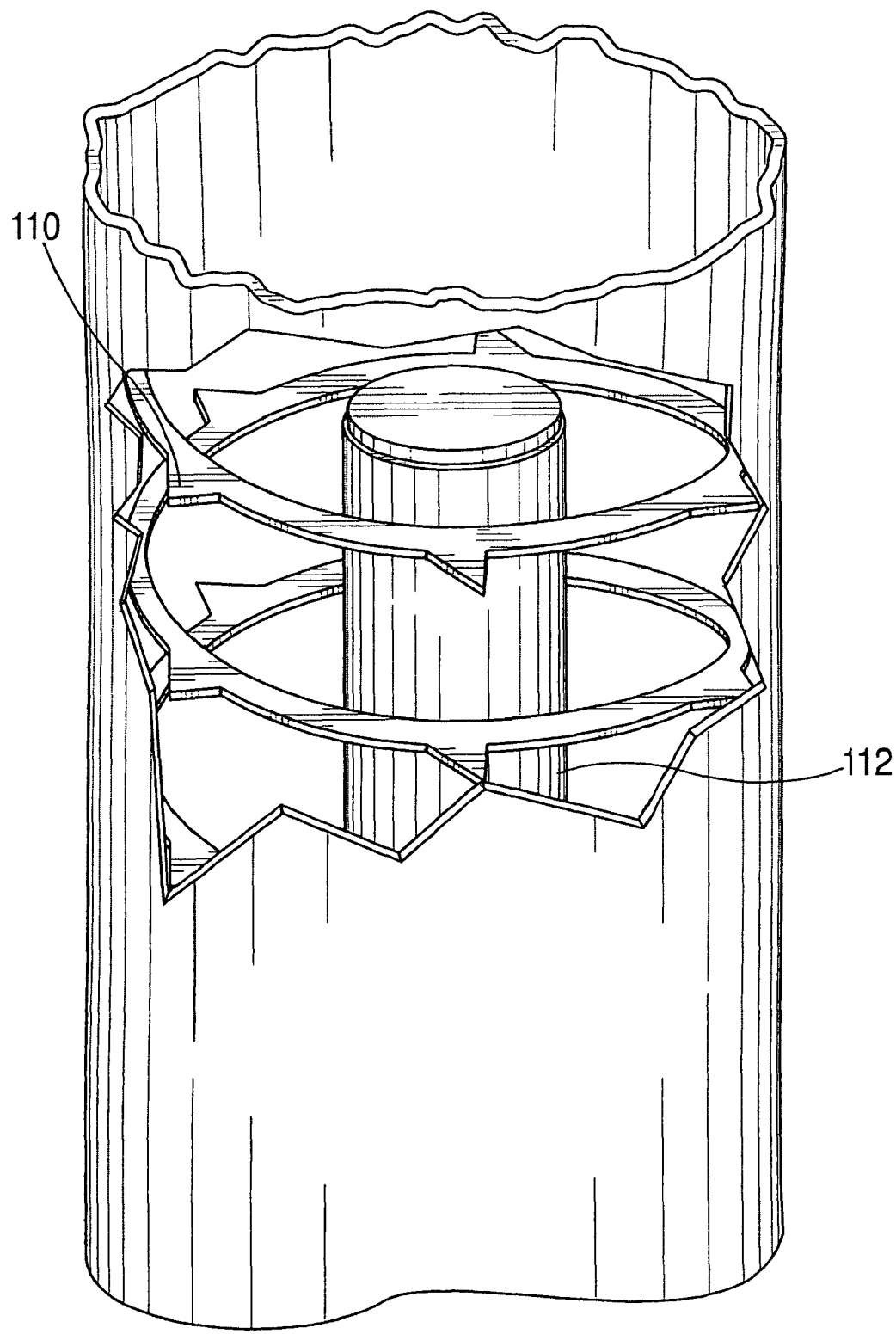
FIG. 23 is a schematic representation showing the spiral coil tack released from the delivery head and fully expanded in the blood vessel.

A preferred delivery method for the fourth described embodiment of the spiral coil tack of FIG. 6 is illustrated in FIGS. 22 and 23. The coil shaped tack in FIG. 6 is formed with barbs and a band with unjoined ends that may or may not have a taper with a varying degrees of thickness along its length. This design is uncoiled in its rest state and looks like a "broken" circle. The coil tack can be compressed to a fraction of its at-rest diameter by pulling its ends in opposite linear directions to form a tight spiral that occupies a smaller-diameter volume so that it can be inserted into the blood vessel. When released it can expand to several times the diameter of its spiral form. FIG. 22 shows multiple units of spiral coil tacks 110 loaded in the interior of the catheter delivery tube 112. When the tack is compressed, it occupies several spiral turns and it spaced out longitudinally. In this case, the delivery catheter is lined with fabric 113 slidable on its interior surface over the end of the tube to its outside (indicated by the pair of U-shaped arrows). As the fabric is pulled through the center of the tube, the tack is advanced toward the end of the delivery catheter. When the tack reaches the end of the delivery catheter, the tack is released from the tube and re-expands to its full size to be deployed into the wall of the blood vessel. FIG. 23 shows the tack deployed in the blood vessel.

In the embodiments described above, the preferred plaque tack device may be made from Nitinol, silicon composite (with or without an inert coating), polyglycolic acid, or some other superelastic material. The anchors can have a preferred length of 0.01 mm to 5 mm. The strip of material can be created from ribbon, round or rectangular wire or a sheet of material processed through photolithographic processing, laser or water cutting, chemical etching or mechanical removal of the final shape, or the use of bottom up fabrication, for instance chemical vapor deposition processes, or the use of injection modeling, hot embossing, or the use of electro or electroless-plating. It may be fabricated from metal, plastic, ceramic, or composite material.

The plaque tack is designed to be inherently self-aligning, i.e., its mechanical installation can accommodate small misalignments. This serves to facilitate placing the tacks in specific locations within diseased blood vessels. With respect to the piercing barb that has a pointed shape, it can be used to embed in objects having irregular surfaces such as plaque or dissected or damaged artery surfaces. After deployment of the plaque tack, the surgeon has the option of placing an angioplasty balloon at the site of the tack and inflating the balloon to press the anchor or anchors into the wall of the blood vessel.

Plaque Tack Design Parameters

The purposes of the plaque tack described herein, as distinct from traditional stenting, are to reduce the amount of implanted foreign material to a minimum while still performing focal treatment of the blood vessel condition so as to cause a minimum of blood vessel wall reaction and adverse post-treatment re-stenosis. The preferred plaque tack is designed to have substantially less metal coverage and/or contact with the blood vessel surface, thereby inciting less acute and chronic inflammation. Reduced pressure of implanted material against the blood vessel wall is correlated with a lower incidence of intimal hyperplasia and better long-term patency. Substantially reduced length along the axial distance of the blood vessel permits a more targeted treatment, correlates with less foreign body coverage of the blood vessel surface, avoids covering portions of the surface that are not in need of coverage, and correlates with both early and late improved patency of blood vessel reconstructions. The plaque tack is deployed only where needed to tack down plaque that has been disrupted by balloon angioplasty or other mechanisms. Rather than cover an entire area of treatment, the plaque tack is placed locally and selectively, and not extending into normal or less diseased artery segments. This permits the blood vessel to retain its natural flexibility because there is a minimal to no scaffolding effect when a small profile tack is used locally or when even multiple tacks are spaced apart over the area of treatment.

One important parameter for design of a plaque tack is having a tack length to diameter (L/D) ratio about equal to or less than 1. That is, the length of the tack along the axis of the blood vessel is about equal to or less than the diameter of the tack. The preferred plaque tack is thus shaped like an annular ring or band, whereas the typical stent is shaped like an elongated tube. The small-profile tack can thus be used locally for targeted treatment of disrupted regions of the blood vessel surface with a minimum of foreign material coverage or contact. Our tests show that a plaque tack with length/diameter ratio ≦1 causes almost no biological reaction or subsequent blood vessel narrowing in comparison to a traditional stent where the length is greater than the diameter, and usually much greater. Our tests indicate that device L/D ≦1 results in a reduction in scaffolding much less than that of the typical stent and causes less arterial wall reaction. For application at sites of small dissection after balloon angioplasty, a plaque tack of minimal footprint may be used such as a single, thin ring-type tack with an L/D ratio in the range of $\frac{1}{10}$ to $\frac{1}{100}$.

Studies on stenting have shown that the length of a stent is correlated with a tendency for occlusion in multiple vascular territories. The more stent length that has been placed, the higher likelihood that the reconstruction will fail. The length of a stent is also directly linked to the frequency and tendency of the stent to break when placed in the superficial femoral artery. The medical literature indicates that the superficial femoral artery performs like a rubber band, and it is likely that changes to the natural elongation and contraction of the superficial femoral artery play a significant role in the failure mode of superficial femoral artery stents. In contrast, the small-profile plaque tack can be implanted only in local areas requiring their use, thereby enabling the blood vessel to retain its natural flexibility to move and bend even after the surface has undergone tacking. Multiple tacks may be implanted separated by regions free of metallic support, thereby leaving the artery free to bend more naturally.

Radial pressure exerted on the blood vessel wall can also be substantially reduced by the small-profile tack design, even when multiple tacks are used in a spaced-apart configuration. To minimize this outward force while still providing the required retention of dissections against the arterial wall, a series of anchor barbs is utilized. The presence of the barbs applying focal pressure to the wall of the artery allows the rest of the tack to apply minimum outward force to the artery wall. The points of the barbs which apply the pressure are very focal, and this is where the most force is applied. The focal nature of the application of the pressure exerted by the tack also minimizes the structural effects of the device. The uniformly distributed focal anchor points provide a distribution of radial energy maximizing the tendency to form a circular lumen.

Another important parameter for design of a plaque tack is the ratio of Vessel Coverage Area (C) to Total Vessel Surface area (TVS). This equation can be applied to one tack device or when several spaced-apart tack devices are placed across the length of a blood vessel treatment area. For a plaque tack, the C/TVS ratio is in the range of about 60% or less, whereas for a stent it can be 100% or more (if applied to overlap the treatment site). For a focal lesion, the conventional treated vessel length is X+10 mm to 20 mm where X is the length of the lesion and the added length is adjoining on normal or less diseased artery. In traditional stenting, the entire treated vessel length would be covered with a stent. For example, in the case of a 2 cm lesion, the treated vessel length would be 3 to 4 cm (usually a single stent of this length would be selected), so that C/TVS is 150%-200%. In contrast, with tack placement, about ½ of X would be covered, and none of the adjoining normal or less diseased artery would be treated. For example, in a 2 cm lesion, approximately 1 cm would be covered, so that the C/TVS ratio is about 60% or less. The key to this innovative approach is placement of bands only in regions of dissections requiring arterial tacking.

Figure 25:
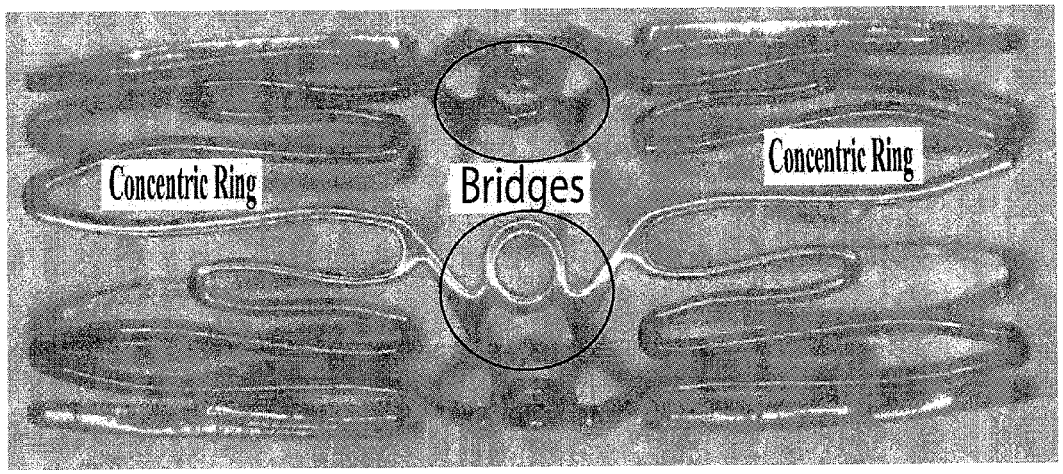
FIG. 25 shows a detailed view of a preferred embodiment of the plaque tack formed with concentric rings connected by a series of bridging members.

In another preferred embodiment, a tack device is formed with concentric side rings or mesh bands connected by longitudinal bridge members. FIG. 25 shows a detailed view of the preferred embodiment of the plaque tack formed with concentric rings on each side connected by a series of bridging members. In the figure the concentric side rings are shown compressed for delivery in the blood vessel. When expanded, the diameter of the tack device is about equal to the width of the tack device. The number of bridging members is chosen depending upon the application. For example, 6 or fewer bridge members may be used between the two concentric rings when desired for limiting neointimal hyperplasia.

The literature in the industry has noted that an important factor in stent design may be the ratio of Relative Metal Surface Area (RMS) compared to the number of longitudinal segments in the device structure, for example, as presented by Mosseri M, Rozenman Y, Mereuta A, Hasin Y, Gotsman M., "New Indicator for Stent Covering Area", in *Catheterization and Cardiovascular Diagnosis*, 1998, v. 445, pp. 188-192. As adapted from the RMS measure, an equation for Effective Metallic Interface (EMI) may be used to compare the embodiment of the tack device with longitudinal bridging members to a typical stent, as follows:

$$EMI = \frac{(1+n^2)C}{\sum_{s=1}^{x}(lw)_s}$$

where x is the number of sections of metal, l is an individual metal section length, w is an individual metal section width, C is the vessel coverage area underneath the device (lumen surface), and n is the number of bridge members longitudinally connected between circumferentially oriented segments. The summation found in the denominator can be interpreted as the total metal surface area. The embodiment of the tack device with longitudinal bridging members has an EMI ≦10, whereas the EMI of a typical stent would be several times greater. This low EMI is due to the nature of the tack design having a small foot-print and minimal longitudinal bridges while a stent typically has a large foot-print and would be a multiple several times that.

Figure 26:
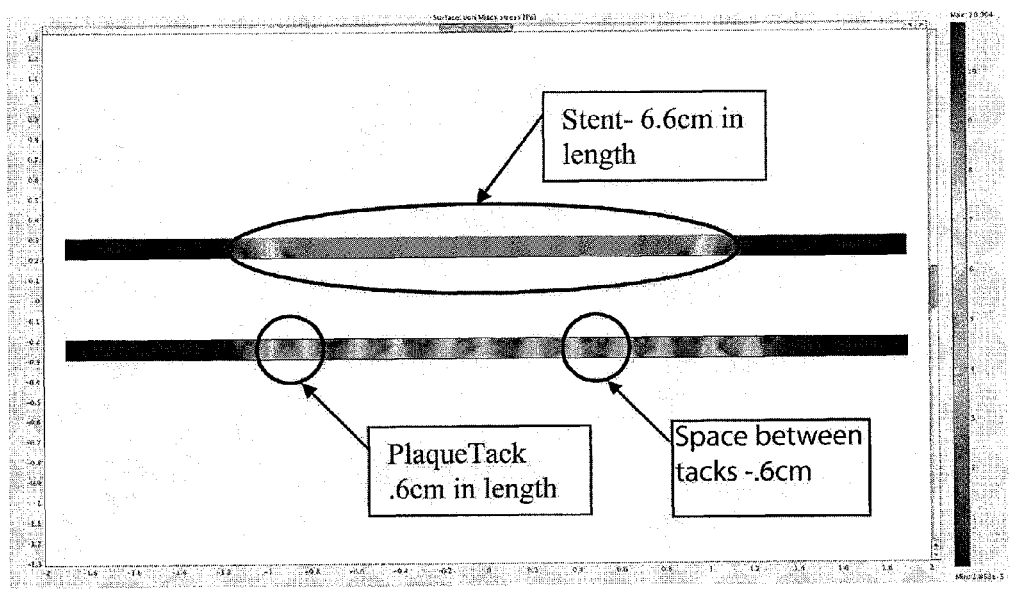
FIG. 26 illustrates the use of multiple tack devices which are spaced apart over the length of a treatment site as compared to a typical stent.

FIG. 26 illustrates the use of multiple tack devices which are spaced apart over the length as compared to a treatment site compared to a typical stent. Preferably, the spacing between tack devices is at least the width of the tack device. Note that the spacing between adjacent tack devices leaves untreated vessel area. A typical stent is shown in the upper part of the figure compared to the use of 6 spaced-apart tack devices at the bottom part of the figure. The overall length of treatment area is 6.6 cm (the same length of the stent) while each band is shown as 6 mm long separated by 6 mm spaces. Therefore, the Vessel Coverage Area for the stent is the same as Total Vessel Surface area (=6.6 cm×0.6π, or 12.44 cm²) which gives a C/TVS ratio of 100%. For the series of spaced-apart tack devices, C is equal to 6×0.6 cm×0.6π, or 6.78 cm², while TVS is 12.44 cm², therefore the C/TVS ratio is equal to 54.5%.

When two or more stents need to be employed over an extended length of treatment site, it has been a conventional practice to overlap adjoining stents to prevent kinking between stents. Due to the increased metal lattice, the region of overlap becomes highly rigid and noncompliant. This noncompliance limits the natural arterial flexibility and increases the tendency for restenosis. Stent fractures occur more frequently in the superficial femoral artery where this bending has a high frequency and are common when multiple stents are deployed and overlap. Stent fractures are associated with a higher risk of in-stent restenosis and re-occlusion. In contrast, the plaque tacks are designed to be applied in local areas and not to be overlapped. Optimal spacing is a minimum of 1 tack width apart for tacks. This permits the artery to maintain its flexibility, and only a half or less of the treated length of the artery will be covered with metal.

Another advantage of using the plaque tack is that the presence of its outer barbs permits the pressure of tack upon the blood vessel wall to be minimized by making the pressure focal and applying low pressure through the barb contact with the wall. The presence of the barbs applying focal pressure to the wall of the artery allows the rest of the tack to apply minimum outward force to the artery wall. The uniformly distributed focal anchor points provide a distribution of radial energy maximizing the tendency to form a circular lumen. Circular lumens offer additional benefit from the standpoint of the vessel wall interaction, independent of the vascular injury.

Use of Plaque Tack after Drug Eluting Balloon Angioplasty

The use of plaque tacks can be combined with use of Drug Eluting Balloon (DEB) angioplasty to manage post angioplasty dissection and avoid the need for stents. In DEB angioplasty, a drug-eluting balloon or a drug coated balloon is prepared in a conventional manner. The drug may be one, or a combination, of biologically active agents that are used for various functions, such as anti-thrombotic, anti-mitotic, anti-proliferative, anti-inflammatory, stimulative of healing, or other functions. The DEB is delivered on a guidewire across an area of blockage or narrowing in the blood vessel system. The DEB is inflated to a specific pressure and for a period of time consistent with the manufactures guidelines of use for treatment purposes, as it pertains the drug coating and the intended outcomes, then the DEB is deflated and removed. At this stage the medication from the DEB has been transferred to the wall of the blood vessel. Intravascular imaging or ultrasound is then used to assess the integrity of the artery and the smoothness of the blood vessel surface at the site where the balloon was inflated. The presence of damage along the surface may be indicated as dissection, elevation of plaque, disruption of tissue, irregularity of surface. In cases where the damage is focal or localized, the plaque tack may be used to tack down the damaged, disrupted, dissected, or irregular blood vessel surface. This permits continuation of a 'stent-free' environment even if damage to the blood vessel has occurred after balloon angioplasty.

At this stage the medication from the DEB has been transferred to the wall of the blood vessel. Contrast is administered into the blood vessel under fluoroscopic guidance or another method such as intravascular ultrasound is used to assess the integrity of the artery and the smoothness of the blood vessel surface at the site where the balloon was inflated. In some cases, one or more of these completion studies will demonstrate the presence of damage along the surface at the site of the balloon inflation. This damage may include dissection, elevation of plaque, disruption of tissue, irregularity of surface.

The plaque tack delivery catheter is loaded with multiple tacks that may be placed at the discretion of the operator, and advanced over a guidewire in the blood vessel to the location where the dissection or disruption or irregularity has occurred. The location is specifically and carefully identified using angiography. The plaque tack(s) is or are deployed at the location(s) of the lesion. More than one tack may be placed to tack down a major dissection. If more than one tack is placed, it may be placed only according to the rules of proper spacing of tacks. That is, the tack should be at least one tack-length apart and do not overlap. After placement of the tack, it may be further expanded into the wall of the blood vessel using a standard angioploasty balloon or a drug-eluting or drug coated balloon. The purpose of the tack is not so much to hold the blood vessel lumen open as to tack down the non-smooth or dissected surface of the blood vessel. This 'touch-up strategy' permits the resolution of the damage created by the drug-eluting or drug coated balloon without resorting to stent placement and thereby maintaining a 'stent-free' environment.

As a further measure, described above, the plaque tack itself can be used to deliver medication to the blood vessel. In addition to the delivery of medication from the barbs, the entire tack can be coated with medication prior to tack placement. The purpose of this activity is to permit the tack to elute biologically active agent or agents that have positive effects on the blood vessel.

It is to be understood that many modifications and variations may be devised given the above description of the principles of the invention. It is intended that all such modifications and variations be considered as within the spirit and scope of this invention, as defined in the following claims.

The invention claimed is:

1. A device for delivering an annular tack into a blood vessel for emplacement against plaque to press and hold it against the blood vessel walls, comprising:
    a catheter delivery tube having a delivery head,
    wherein the annular tack is to be made of a material having shape-memory and formed as a linear strip ribbon in its rest state and is capable of restoring to an annular shape when exposed to internal body temperature,
    wherein the delivery head of the catheter delivery tube has a plurality of barrels of a rotatable, multi-barreled tack magazine for loading a plurality of annular tacks therein in an array around the outer surface of the catheter delivery tube, and an internal pressure chamber for generating pressure for ejecting a ribbon strip from its barrel as it is moved by rotation of the magazine to bring each ribbon strip in turn to an ejector position in the delivery head.

2. The device of claim 1, wherein the delivery head has an ejector track with a curved outlet tunnel for bending the ribbon strip towards its annular shape as the delivery head rotates.

3. The device of claim 2, wherein the curved outlet tunnel is adapted to capture the end of the ribbon strip pushed into the ejector track and cause a middle part of the ribbon strip to bulge outward toward the blood vessel wall with the rotation of the delivery head.

4. The device of claim 1, wherein the delivery device is configured to cause the annular tack to lay down perpendicular to a longitudinal axis of the blood vessel.

5. The device of claim 1, wherein the delivery head is configured such that rotation of the delivery head causes the annular tack to be laid down annularly spanning a wall of the blood vessel.

6. The device of claim 1, further comprising the annular tack wherein the annular tack has a first portion and a second portion wherein the annular tack is configured such that the first portion overlays the second portion when in the annular shape.

7. A device for delivering an annular tack into an anatomical structure, comprising:
    a catheter delivery tube having a delivery head,
    wherein the annular tack has a first linear position and a second annular position, wherein the delivery head of the catheter delivery tube has a plurality of barrels of a rotatable, multi-barreled tack magazine for loading a plurality of annular tacks therein in an array around the outer surface of the catheter delivery tube, and an internal pressure chamber for generating pressure to eject an annular tack in its first linear position from its barrel as it is moved by rotation of the magazine to bring each annular tack in turn to an ejector position in the delivery head.

8. The device of claim 7, wherein the delivery head has an ejector track with a curved outlet tunnel for bending the ribbon strip towards its second annular shape as the delivery head rotates.

9. The device of claim 8, wherein the curved outlet tunnel is adapted to capture the end of the ribbon strip pushed into the ejector track and cause a middle part of the ribbon strip to bulge outward toward the wall of the anatomical structure with the rotation of the delivery head.

10. The device of claim 7, wherein the anatomical structure is a blood vessel and wherein the delivery device is configured to cause the annular tack to lay down perpendicular to a longitudinal axis of the blood vessel.

11. The device of claim 7, further comprising the annular tack wherein the annular tack has a first portion and a second portion wherein the annular tack is configured such that the first portion overlays the second portion when in the annular shape.

12. The device of claim 8, wherein the outlet tunnel curves from an axial direction of the catheter to the radial direction facing toward a wall of the anatomical structure.

* * * * *